United States Patent
Vanoli

(10) Patent No.: US 10,631,491 B2
(45) Date of Patent: Apr. 28, 2020

(54) LETTUCE VARIETY 'HERCULES'

(71) Applicant: Pinnacle Seed, Inc., Carmel, CA (US)

(72) Inventor: Mike Vanoli, Carmel, CA (US)

(73) Assignee: Pinnacle Seed, Inc., Carmel, CA (US)

( * ) Notice: Subject to any disclaimer, the term of this patent is extended or adjusted under 35 U.S.C. 154(b) by 0 days.

(21) Appl. No.: 16/135,358

(22) Filed: Sep. 19, 2018

(65) Prior Publication Data
US 2019/0053455 A1 Feb. 21, 2019

Related U.S. Application Data

(63) Continuation of application No. 15/616,859, filed on Jun. 7, 2017, now Pat. No. 10,123,502.

(60) Provisional application No. 62/346,916, filed on Jun. 7, 2016.

(51) Int. Cl.
*A01H 6/14* (2018.01)
*A01H 5/12* (2018.01)

(52) U.S. Cl.
CPC .............. *A01H 5/12* (2013.01); *A01H 6/1472* (2018.05)

(58) Field of Classification Search
None
See application file for complete search history.

(56) References Cited

U.S. PATENT DOCUMENTS

| 8,362,326 B2 | 1/2013 | Bellec |
| 8,404,937 B2 * | 3/2013 | Gibson .................... A01H 5/12 435/410 |
| 8,476,498 B2 | 7/2013 | Peng |
| 10,123,502 B2 | 11/2018 | Vanoli |
| 2017/0347614 A1 | 12/2017 | Vanoli |

OTHER PUBLICATIONS

Liu et al., (1999). "First Report of Tomato Bushy Stunt Virus Isolated from Lettuce," Plant Disease, 83(3):301.
Nagata, R. T. (1992). "Clip and Wash Method of Emasculation for Lettuce," Hortscience 27(8):907-908.
Obermeier et al., (2001). "Characterization of Distinct Tombusviruses that Cause Diseases of Lettuce and Tomato in the Western United States," Phytopathology, 91(8): 797-806.
Ryder et al.,(1974). "Mist depollination of lettuce flowers," Hortscience, 9:584.
Non-Final Office Action received for U.S. Appl. No. 15/616,859, dated Apr. 5, 2018, 12 pages.
Unpublished U.S. Appl. No. 16/420,069, filed May 22, 2019, titled "Lettuce Varieties." (Copy not submitted herewith pursuant to the waiver of 37 C.F.R. § 1.98(a)(2)(iii)).

* cited by examiner

*Primary Examiner* — Eileen B O Hara
(74) *Attorney, Agent, or Firm* — Morrison & Foerster LLP

(57) ABSTRACT

New lettuce variety designated 'Hercules' is described. 'Hercules' is a lettuce variety exhibiting stability and uniformity.

17 Claims, 27 Drawing Sheets
(27 of 27 Drawing Sheet(s) Filed in Color)

LETTUCE VARIETY 'HERCULES'

CROSS-REFERENCE TO RELATED APPLICATION

This application is a continuation of U.S. application Ser. No. 15/616,859, filed Jun. 7, 2017, which claims the benefit of U.S. Provisional Application No. 62/346,916, filed Jun. 7, 2016, which are hereby incorporated by reference in their entirety.

FIELD

This invention relates to the field of plant breeding. In particular, this invention relates to new lettuce, *Lactuca sativa*, variety 'Hercules'.

BACKGROUND

Lettuce is an increasingly popular crop. Worldwide lettuce consumption continues to increase. As a result of this demand, there is a continued need for new lettuce varieties. In particular, there is a need for improved green leaf and iceberg lettuce varieties that exhibit improved growth habits, bolting and tip burn tolerance, and disease resistance.

SUMMARY

In order to meet these needs, the present invention is directed to improved lettuce varieties.

As used herein lettuce variety 'Canyon' is the same lettuce variety as lettuce variety 'Mammoth' having ATCC Accession Number X8 and disclosed in U.S. Provisional Application No. 62/346,916. While the name has changed, lettuce variety 'Canyon' has all the defining characteristics of lettuce variety 'Mammoth'.

As used herein lettuce variety 'Hercules' is the same lettuce variety as lettuce variety 'Navigator' having ATCC Accession Number PTA-126296 and disclosed in U.S. Provisional Application No. 62/346,916. While the name has changed, lettuce variety 'Hercules' has all the defining characteristics of lettuce variety 'Navigator'.

In one embodiment, the present invention is directed to lettuce, *Lactuca sativa*, seed designated as 'Wheelhouse'. In one embodiment, the present invention is directed to a *Lactuca sativa* lettuce plant and parts isolated therefrom produced by growing 'Wheelhouse' lettuce seed. In another embodiment, the present invention is directed to a *Lactuca sativa* plant and parts isolated therefrom having all the physiological and morphological characteristics of a *Lactuca sativa* plant produced by growing 'Wheelhouse' lettuce seed. In still another embodiment, the present invention is directed to an $F_1$ hybrid *Lactuca sativa* lettuce seed, plants grown from the seed, and a head isolated therefrom having 'Wheelhouse' as a parent, where 'Wheelhouse' is grown from 'Wheelhouse'.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Wheelhouse' lettuce plants. In another embodiment, the present invention is further directed to tissue culture of 'Wheelhouse' lettuce plants, and to lettuce plants regenerated from the tissue culture, where the plant has all of the morphological and physiological characteristics of 'Wheelhouse' lettuce plants.

The present invention is further directed to a method of selecting lettuce plants by: a) growing more than one 'Wheelhouse' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Wheelhouse' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Trailblazer'. In one embodiment, the present invention is directed to a *Lactuca sativa* lettuce plant and parts isolated therefrom produced by growing 'Trailblazer' lettuce seed. In another embodiment, the present invention is directed to a *Lactuca sativa* plant and parts isolated therefrom having all the physiological and morphological characteristics of a *Lactuca sativa* plant produced by growing 'Trailblazer' lettuce seed. In still another embodiment, the present invention is directed to an $F_1$ hybrid *Lactuca sativa* lettuce seed, plants grown from the seed, and a head isolated therefrom having 'Trailblazer' as a parent, where 'Trailblazer' is grown from 'Trailblazer' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Trailblazer' lettuce plants. In another embodiment, the present invention is further directed to tissue culture of 'Trailblazer' lettuce plants, and to lettuce plants regenerated from the tissue culture, where the plant has all of the morphological and physiological characteristics of 'Trailblazer' lettuce plants.

The present invention is further directed to a method of selecting lettuce plants by: a) growing more than one 'Trailblazer' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Trailblazer' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as 'Haymaker' having ATCC Accession Number PTA-125104. In one embodiment, the present invention is directed to a *Lactuca sativa* lettuce plant and parts isolated therefrom produced by growing 'Haymaker' lettuce seed. In another embodiment, the present invention is directed to a *Lactuca sativa* plant and parts isolated therefrom having all the physiological and morphological characteristics of a *Lactuca sativa* plant produced by growing 'Haymaker' lettuce seed having ATCC Accession Number PTA-125104. In still another embodiment, the present invention is directed to an $F_1$ hybrid

*Lactuca sativa* lettuce seed, plants grown from the seed, and a head isolated therefrom having 'Haymaker' as a parent, where 'Haymaker' is grown from 'Haymaker' lettuce seed having ATCC Accession Number PTA-125104.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Haymaker' lettuce plants. In another embodiment, the present invention is further directed to tissue culture of 'Haymaker' lettuce plants, and to lettuce plants regenerated from the tissue culture, where the plant has all of the morphological and physiological characteristics of 'Haymaker' lettuce plants.

The present invention is further directed to a method of selecting lettuce plants by: a) growing more than one 'Haymaker' lettuce plant, where the plants are grown from lettuce seed having ATCC Accession Number PTA-125104; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Haymaker' lettuce seed having ATCC Accession Number PTA-125104. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as '14RDSJV055-1'. In one embodiment, the present invention is directed to a *Lactuca sativa* lettuce plant and parts isolated therefrom produced by growing '14RDSJV055-1' lettuce seed. In another embodiment, the present invention is directed to a *Lactuca sativa* plant and parts isolated therefrom having all the physiological and morphological characteristics of a *Lactuca sativa* plant produced by growing '14RDSJV055-1' lettuce seed. In still another embodiment, the present invention is directed to an $F_1$ hybrid *Lactuca sativa* lettuce seed, plants grown from the seed, and a head isolated therefrom having '14RDSJV055-1' as a parent, where '14RDSJV055-1' is grown from '14RDSJV055-1' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from '14RDSJV055-1' lettuce plants. In another embodiment, the present invention is further directed to tissue culture of '14RDSJV055-1' lettuce plants, and to lettuce plants regenerated from the tissue culture, where the plant has all of the morphological and physiological characteristics of '14RDSJV055-1' lettuce plants.

The present invention is further directed to a method of selecting lettuce plants by: a) growing more than one '14RDSJV055-1' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from '14RDSJV055-1' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as '14RDSJV055-3'. In one embodiment, the present invention is directed to a *Lactuca sativa* lettuce plant and parts isolated therefrom produced by growing '14RDSJV055-3' lettuce seed. In another embodiment, the present invention is directed to a *Lactuca sativa* plant and parts isolated therefrom having all the physiological and morphological characteristics of a *Lactuca sativa* plant produced by growing '14RDSJV055-3' lettuce seed. In still another embodiment, the present invention is directed to an $F_1$ hybrid *Lactuca sativa* lettuce seed, plants grown from the seed, and a head isolated therefrom having '14RDSJV055-3' as a parent, where '14RDSJV055-3' is grown from '14RDSJV055-3' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from '14RDSJV055-3' lettuce plants. In another embodiment, the present invention is further directed to tissue culture of '14RDSJV055-3' lettuce plants, and to lettuce plants regenerated from the tissue culture, where the plant has all of the morphological and physiological characteristics of '14RDSJV055-3' lettuce plants.

The present invention is further directed to a method of selecting lettuce plants by: a) growing more than one '14RDSJV055-3' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from '14RDSJV055-3' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, *Lactuca sativa*, seed designated as '14RDSJV055-7'. In one embodiment, the present invention is directed to a *Lactuca sativa* lettuce plant and parts isolated therefrom produced by growing '14RDSJV055-7' lettuce seed. In another embodiment, the present invention is directed to a *Lactuca sativa* plant and parts isolated therefrom having all the physiological and morphological characteristics of a *Lactuca sativa* plant produced by growing '14RDSJV055-7' lettuce seed. In still another embodiment, the present invention is directed to an $F_1$ hybrid *Lactuca sativa* lettuce seed, plants grown from the seed, and a head isolated therefrom having '14RDSJV055-7' as a parent, where '14RDSJV055-7' is grown from '14RDSJV055-7' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from '14RDSJV055-7' lettuce plants. In another embodiment, the present invention is further directed to tissue culture of '14RDSJV055-7' lettuce plants, and to lettuce plants regenerated from the tissue culture, where the plant has all of the morphological and physiological characteristics of '14RDSJV055-7' lettuce plants.

The present invention is further directed to a method of selecting lettuce plants by: a) growing more than one '14RDSJV055-7' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from '14RDSJV055-7' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, Lactuca sativa, seed designated as 'Canyon'. In one embodiment, the present invention is directed to a Lactuca sativa lettuce plant and parts isolated therefrom produced by growing 'Canyon' lettuce seed. In another embodiment, the present invention is directed to a Lactuca sativa plant and parts isolated therefrom having all the physiological and morphological characteristics of a Lactuca sativa plant produced by growing 'Canyon' lettuce seed. In still another embodiment, the present invention is directed to an $F_1$ hybrid Lactuca sativa lettuce seed, plants grown from the seed, and a head isolated therefrom having 'Canyon' as a parent, where 'Canyon' is grown from 'Canyon' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Canyon' lettuce plants. In another embodiment, the present invention is further directed to tissue culture of 'Canyon' lettuce plants, and to lettuce plants regenerated from the tissue culture, where the plant has all of the morphological and physiological characteristics of 'Canyon' lettuce plants.

The present invention is further directed to a method of selecting lettuce plants by: a) growing more than one 'Canyon' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Canyon' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, Lactuca sativa, seed designated as 'PS1102B'. In one embodiment, the present invention is directed to a Lactuca sativa lettuce plant and parts isolated therefrom produced by growing 'PS1102B' lettuce seed. In another embodiment, the present invention is directed to a Lactuca sativa plant and parts isolated therefrom having all the physiological and morphological characteristics of a Lactuca sativa plant produced by growing 'PS1102B' lettuce seed. In still another embodiment, the present invention is directed to an $F_1$ hybrid Lactuca sativa lettuce seed, plants grown from the seed, and a head isolated therefrom having 'PS1102B' as a parent, where 'PS1102B' is grown from 'PS1102B' lettuce seed.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'PS1102B' lettuce plants. In another embodiment, the present invention is further directed to tissue culture of 'PS1102B' lettuce plants, and to lettuce plants regenerated from the tissue culture, where the plant has all of the morphological and physiological characteristics of 'PS1102B' lettuce plants.

The present invention is further directed to a method of selecting lettuce plants by: a) growing more than one 'PS1102B' lettuce plant, where the plants are grown from lettuce seed; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'PS1102B' lettuce seed. In still another embodiment, the present invention is further directed to lettuce plants, lettuce parts from the lettuce plants (e.g., lettuce heads), and seeds produced therefrom where the lettuce plant is isolated by the breeding method of the invention.

In one embodiment, the present invention is directed to lettuce, Lactuca sativa, seed designated as 'Hercules' having ATCC Accession Number PTA-126296. In one embodiment, the present invention is directed to a Lactuca sativa lettuce plant and parts isolated therefrom produced by growing 'Hercules' lettuce seed. In another embodiment, the present invention is directed to a Lactuca sativa plant and parts isolated therefrom having all the physiological and morphological characteristics of a Lactuca sativa plant produced by growing 'Hercules' lettuce seed having ATCC Accession Number PTA-126296. In still another embodiment, the present invention is directed to an $F_1$ hybrid Lactuca sativa lettuce seed, plants grown from the seed, and a head isolated therefrom having 'Hercules' as a parent, where 'Hercules' is grown from 'Hercules' lettuce seed having ATCC Accession Number PTA-126296.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Hercules' lettuce plants. In another embodiment, the present invention is further directed to tissue culture of 'Hercules' lettuce plants, and to lettuce plants regenerated from the tissue culture, where the plant has all of the morphological and physiological characteristics of 'Hercules' lettuce plants.

The present invention is further directed to a method of selecting lettuce plants by: a) growing more than one 'Hercules' lettuce plant, where the plants are grown from lettuce seed having ATCC Accession Number PTA-126296; and b) selecting a plant from step a). The present invention is further directed to lettuce plants and seeds produced therefrom, where the lettuce plants and seeds are isolated by the selection method of the invention.

In another embodiment, the present invention is further directed to a method of breeding lettuce plants by crossing a lettuce plant with a plant grown from 'Hercules' lettuce seed having ATCC Accession Number PTA-126296. In still another embodiment, the present invention is further directed to lettuce plants, lettuce parts from the lettuce plants (e.g., lettuce heads), and seeds produced therefrom where the lettuce plant is isolated by the breeding method of the invention.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1 shows a bottom view of lettuce heads.

FIG. 2 shows a cross-sectional view of lettuce heads.

FIG. 3A shows a top view of a plant of lettuce variety 'Wheelhouse'. FIG. 3B shows a top view of a plant of lettuce variety 'Gilaben'.

FIG. 4A shows a flowering plant of lettuce variety 'Wheelhouse'. FIG. 4B shows a flowering plant of lettuce variety 'Gilaben'.

FIG. 5A shows a seedling of lettuce variety 'Wheelhouse'. FIG. 5B shows a seedling of lettuce variety 'Gilaben'. FIG. 5C shows a comparison of leaflets of lettuce varieties 'Wheelhouse' and 'Gilaben'.

FIG. 6A shows a top view of plants of lettuce variety 'Trailblazer'. FIG. 6B shows a top view of plants of lettuce variety 'Mammoth'.

FIG. 7A shows bolting plants of lettuce variety 'Trailblazer'. FIG. 7B shows bolting plants of lettuce variety 'Mammoth'.

FIG. 8A shows flowering plants of lettuce variety 'Trailblazer'. FIG. 8B shows flowering plants of lettuce variety 'Mammoth'.

FIG. 9A shows a seedling of lettuce variety 'Trailblazer'. FIG. 9B shows a seedling of lettuce variety 'Mammoth'. FIG. 9C shows a comparison of leaflets of lettuce varieties 'Trailblazer' and 'Mammoth'.

FIG. 10A shows a side view of heads of lettuce varieties 'Haymaker' and 'Venus'. FIG. 10B shows a top view of heads of lettuce varieties 'Haymaker' and 'Venus'. FIG. 10C shows a cross-sectional view of heads of lettuce varieties 'Haymaker' and 'Venus'. FIG. 10D shows a bottom view of heads of lettuce varieties 'Haymaker' and 'Venus'.

FIG. 11A shows flowering plants of lettuce variety 'Haymaker'. FIG. 11B shows flowering plants of lettuce variety 'Venus'.

FIG. 12A shows a seedling of lettuce variety 'Haymaker'. FIG. 12B shows a seedling of lettuce variety 'Venus'. FIG. 12C shows a comparison of leaflets of lettuce varieties 'Haymaker' and 'Venus'.

FIG. 13A shows a top view of heads of lettuce variety '14RDSJV055-1'. FIG. 13B shows a top view of heads of lettuce variety '14RDSJV055-3'. FIG. 13C shows a top view of heads of lettuce variety '14RDSJV055-7'. FIG. 13D shows a top view of heads of lettuce variety 'Oso Verde'.

FIG. 14A shows rows of plants of lettuce variety '14RDSJV055-1'. FIG. 14B shows rows of plants of lettuce variety '14RDSJV055-3'. FIG. 14C shows rows of plants of lettuce variety '14RDSJV055-7'. FIG. 14D shows rows of plants of lettuce variety 'Oso Verde'.

FIG. 15A shows flowering plants of lettuce variety '14RDSJV055-1'. FIG. 15B shows flowering plants of lettuce variety '14RDSJV055-3'. FIG. 15C shows flowering plants of lettuce variety '14RDSJV055-7'. FIG. 15D shows flowering plants of lettuce variety 'Oso Verde'.

FIG. 16A shows a seedling of lettuce variety '14RDSJV055-1'. FIG. 16B shows a seedling of lettuce variety '14RDSJV055-3'. FIG. 16C shows a seedling of lettuce variety '14RDSJV055-7'. FIG. 16D shows a seedling of lettuce variety 'Oso Verde'.

FIG. 18A shows a comparison of leaves of lettuce varieties 'PS1102B' and 'Bondi'. FIG. 18B shows a comparison of a top view of heads of lettuce varieties 'PS1102B' and 'Bondi'. FIG. 18C shows a comparison of a bottom view of heads of lettuce varieties 'PS1102B' and 'Bondi'. FIG. 18D shows a comparison of a side view of heads of lettuce varieties 'PS1102B' and 'Bondi'. FIG. 18E shows a comparison of a cross-sectional view of heads of lettuce varieties 'PS1102B' and 'Bondi'.

FIG. 19A shows flowering plants of lettuce variety 'PS1102B'. FIG. 19B shows flowering plants of lettuce variety 'Bondi'.

FIG. 20A shows a seedling of lettuce variety 'PS1102B'. FIG. 20B shows a seedling of lettuce variety 'Bondi'. FIG. 20C shows a comparison of leaflets of lettuce varieties 'PS1102B' and 'Bondi'.

FIG. 21A shows a top view of plants of lettuce variety 'Canyon'. FIG. 21B shows a top view of plants of lettuce variety 'Hercules'. FIG. 21C shows a top view of plants of lettuce variety 'Regency'.

FIG. 22A shows a bottom view of a head of lettuce variety 'Canyon'. FIG. 22B shows a bottom view of a head of lettuce variety 'Hercules'. FIG. 22C shows a bottom view of a head of lettuce variety 'Regency'.

FIG. 23A shows a cross-sectional view of a head of lettuce variety 'Canyon'. FIG. 23B shows a cross-sectional view of a head of lettuce variety 'Hercules'. FIG. 23C shows a cross-sectional view of a head of lettuce variety 'Regency'.

FIG. 24A shows a flowering plant of lettuce variety 'Canyon'. FIG. 24B shows a flowering plant of lettuce variety 'Hercules'. FIG. 24C shows a flowering plant of lettuce variety 'Regency'.

FIG. 25A shows a seedling of lettuce variety 'Canyon'. FIG. 25B shows a seedling of lettuce variety 'Hercules'. FIG. 25C shows a seedling of lettuce variety 'Regency'.

DETAILED DESCRIPTION

Definitions

Figure 1:
FIG. 1 shows a comparison of heads between lettuce varieties 'Wheelhouse' and 'Gilaben'.
Figure 2:
FIG. 2 shows a comparison of heads between lettuce varieties 'Wheelhouse' and 'Gilaben'.
Figure 3A:
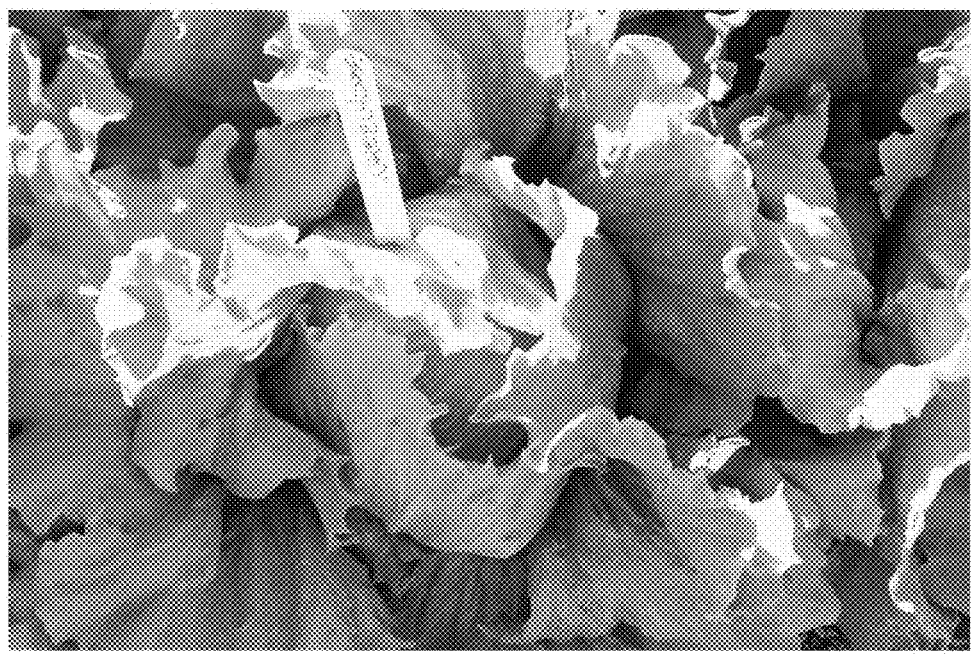
FIGS. 3A and 3B show a comparison between lettuce varieties 'Wheelhouse' and 'Gilaben'.
Figure 3B:
Figure 4A:
FIGS. 4A and 4B show a comparison between lettuce varieties 'Wheelhouse' and 'Gilaben'.
Figure 4B:
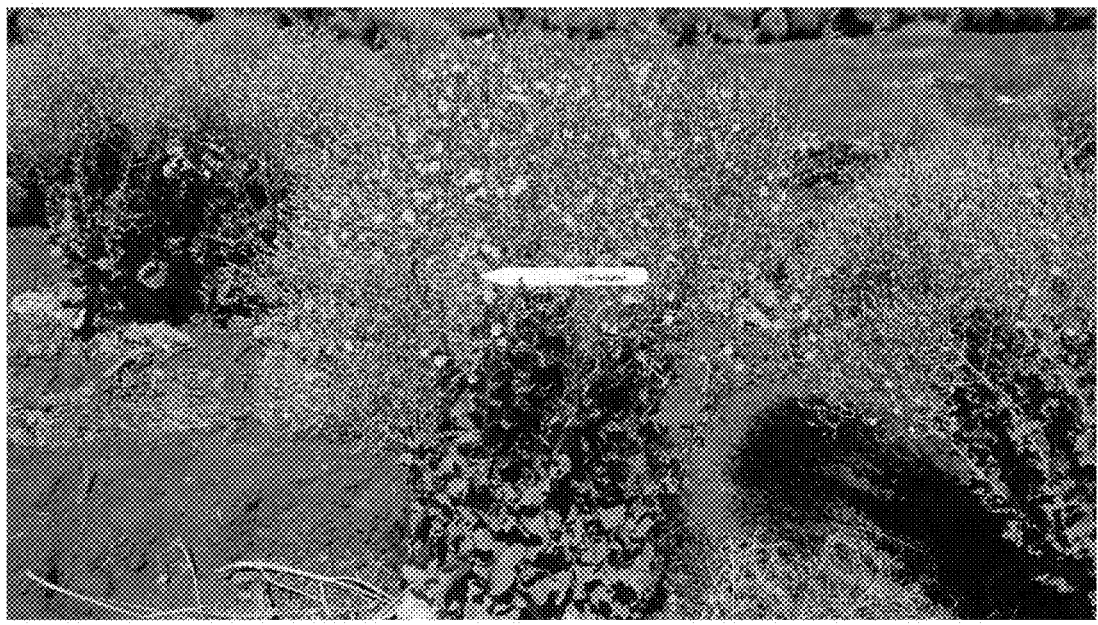
Figure 5A:
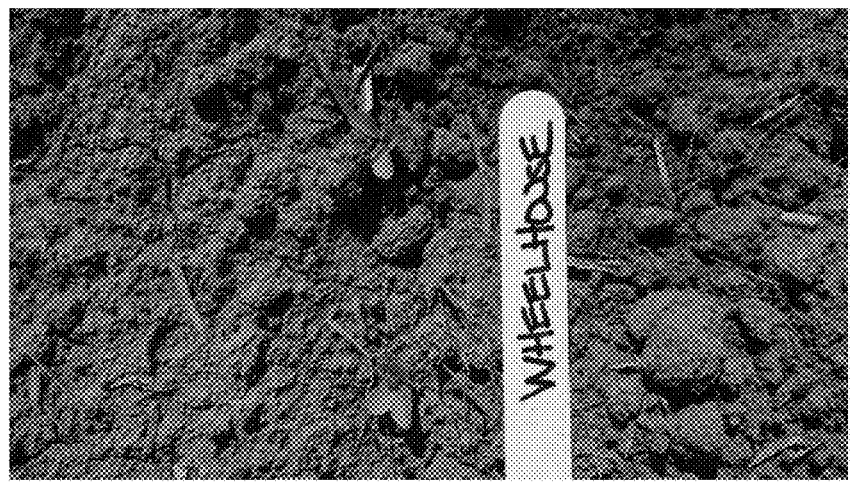
FIGS. 5A, 5B, and 5C show a comparison between lettuce varieties 'Wheelhouse' and 'Gilaben'.
Figure 5B:
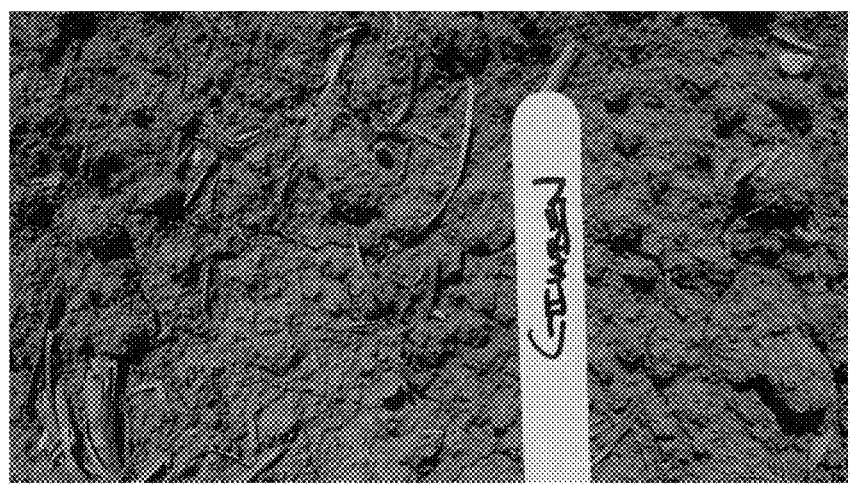
Figure 5C:
Figure 6A:
FIGS. 6A and 6B show a comparison between lettuce varieties 'Trailblazer' and 'Mammoth'.
Figure 6B:
Figure 7A:
FIGS. 7A and 7B show a comparison between lettuce varieties 'Trailblazer' and 'Mammoth'.
Figure 7B:
Figure 8A:
FIGS. 8A and 8B show a comparison between lettuce varieties 'Trailblazer' and 'Mammoth'.
Figure 8B:
Figure 9A:
FIGS. 9A, 9B, and 9C show a comparison between lettuce varieties 'Trailblazer' and 'Mammoth'.
Figure 9B:
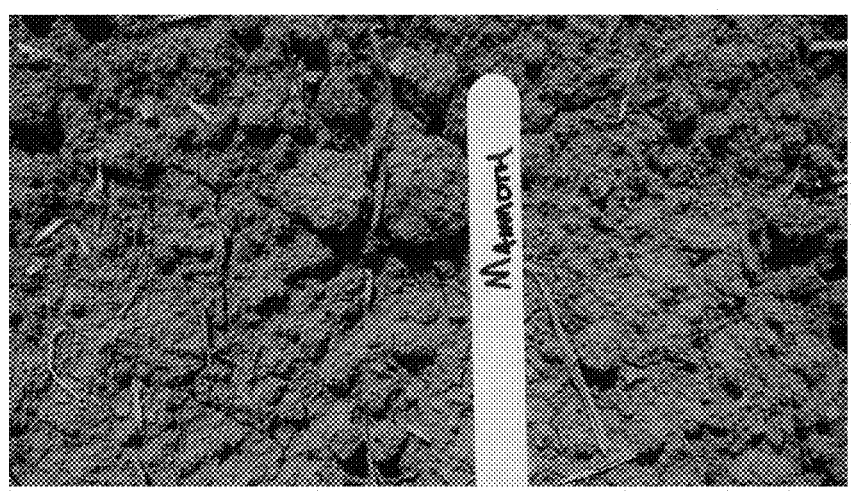
Figure 9C:
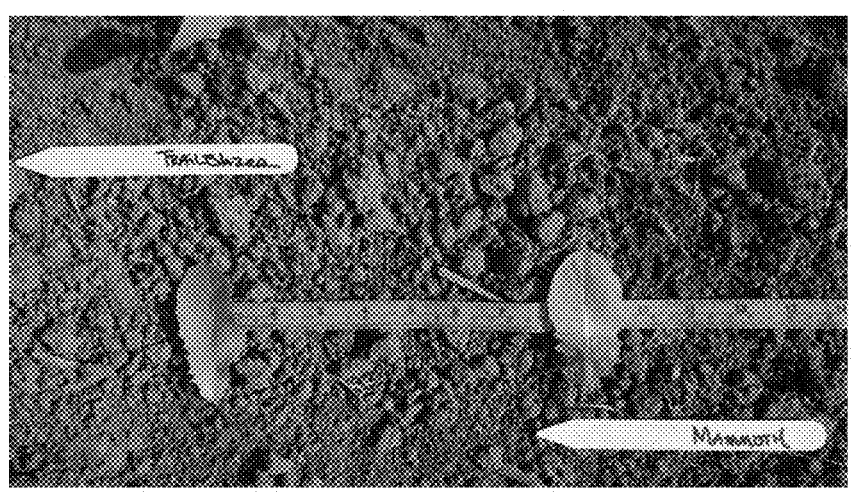
Figure 10A:
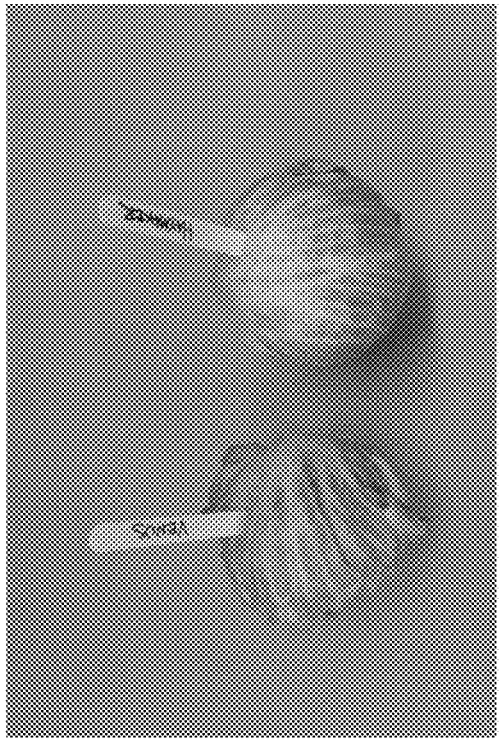
FIGS. 10A, 10B, 10C, and 10D show a comparison between lettuce varieties 'Haymaker' and 'Venus'.
Figure 10B:
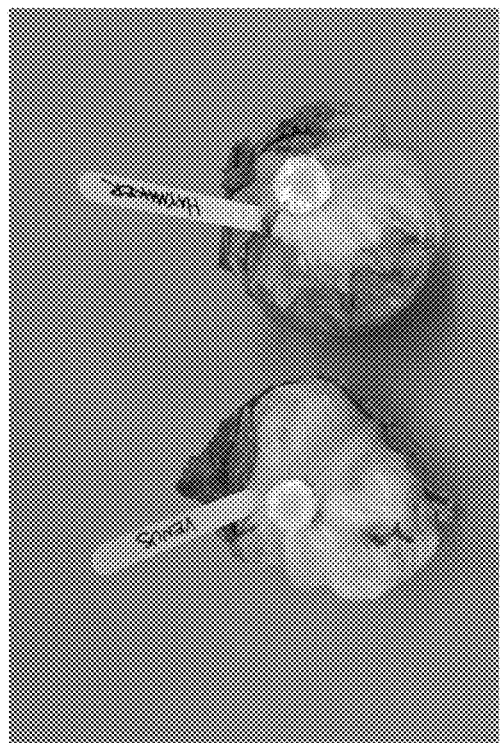
Figure 10C:
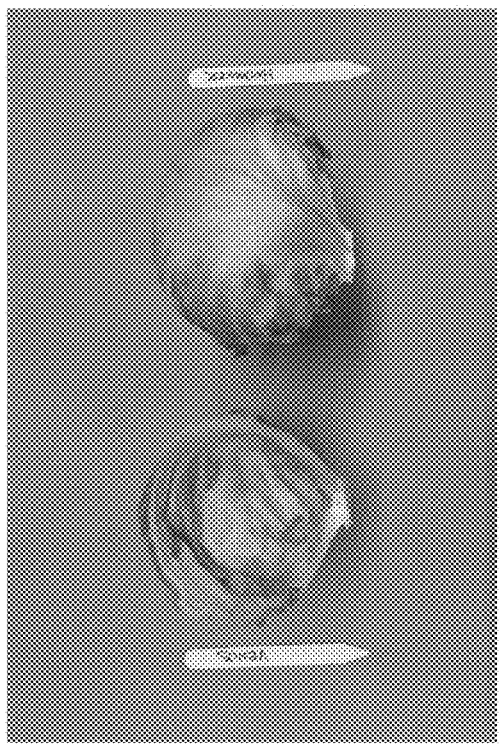
Figure 10D:
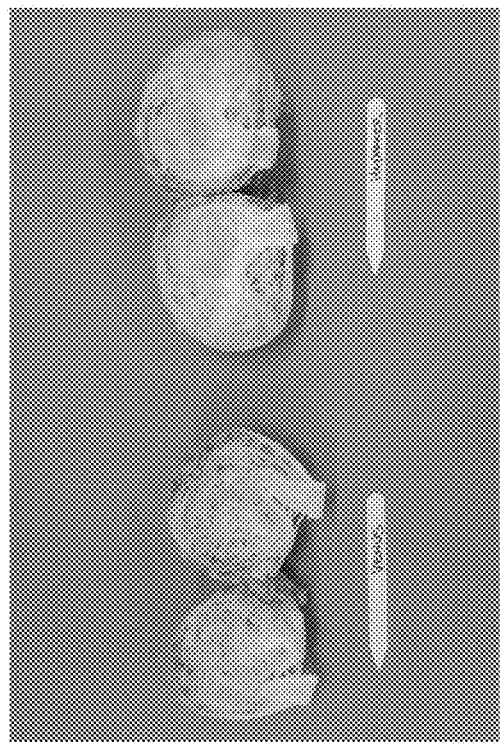

In order to more clearly understand the invention, the following definitions are provided:

Core Length: Core length is the length of the internal lettuce stem. Core length is measured from the base of the cut head to the tip of the core.

Core Diameter: Core diameter is the diameter of the lettuce stem at the base of the cut head.

Heart Length: Heart length is the length of the vertically sliced lettuce plant as measured from the base of the cut stem to the top leaf margin of the longest outermost leaf that encloses the green leaf heart.

Plant Diameter: The plant diameter is a measurement across the top of the lettuce plant at its widest point. The measurement of frame diameter is taken from the outer most leaf tip horizontally to the outer most leaf tip.

Head Diameter: Head diameter is the diameter of the vertically sliced lettuce plant head at its widest horizontal point, perpendicular to the stem.

Head Length: Head length is the diameter of the vertically sliced lettuce plant head as measured from the base of the cut stem to the cap leaf.

Head Weight: Head weight is the weight of the marketable lettuce plant, cut and trimmed to market specifications.

Lettuce Mosaic Virus: A disease that can cause a stunted, deformed, or mottled pattern in young lettuce and yellow, twisted, and deformed leaves in older lettuce.

Maturity Date: Maturity refers to the stage when the plants are of full size or optimum weight, in marketable form or shape to be of commercial or economic value.

*Nasonovia ribisnigri*: A lettuce aphid that colonizes the innermost leaves of the lettuce plant, contaminating areas that cannot be treated easily with insecticides.

Tip burn: Means a browning of the edges or tips of lettuce leaves that is a physiological response to a lack of calcium.

Tomato Bushy Stunt: Lettuce dieback was first observed in California in the mid-1980s, and reports of the disease have increased over the last 10 years. Complete crop losses have occurred in fields of Green Leaf lettuce, and no commercial Green Leaf cultivar has been shown to be resistant to the disease. In the U.S., Green Leaf is a rapidly growing market segment, having increased 68% over the last five years (USDA, 2002). The disease has occurred in commercial fields of some leaf lettuce cultivars; however, symptoms have never been observed on any modern crisp-head (iceberg) cultivars. Lettuce dieback is caused by several related tombusviruses including tomato bushy stunt virus (TBSV) and lettuce necrotic stunt virus (LNSV) (Liu et al., 1999; Obermeier et al., 2001). These are soil-borne, highly stable, and mechanically transmitted, and have no known vector. The conditions affecting symptom development remain poorly understood. The disease is frequently observed in low-lying areas of fields with a prior history of flooding, suggesting that the virus may be carried in river water and/or that disease symptoms may be associated with increased root stresses such as those presented by excess moisture. No effective cultural or chemical control methods have yet been identified.

Resistance to Tomato Busy Stunt refers to a level of resistance in a lettuce variety as measured by visual symptoms. Resistance is deemed present when symptoms are not present in at least 95% of a lettuce variety when exposed to tomato bushy stunt virus (TBSV).

Taking into account these definitions, the present invention is directed to seeds of the lettuce varieties 'Wheelhouse', 'Trailblazer', 'Haymaker', '14RDSJV055-1', '14RDSJV055-3', '14RDSJV055-7', 'PS1102B', 'Hercules', and 'Canyon', plants produced by growing 'Wheelhouse', 'Trailblazer', 'Haymaker', '14RDSJV055-1', '14RDSJV055-3', '14RDSJV055-7', 'PS1102B', 'Hercules', and/or 'Canyon' lettuce seeds, heads isolated or harvested from the plants, one or more plants selected from a collection of 'Wheelhouse', 'Trailblazer', 'Haymaker', '14RDSJV055-1', '14RDSJV055-3', '14RDSJV055-7', 'PS1102B', 'Hercules', and/or 'Canyon' plants and seeds derived or produced therefrom; plants produced by crossing a lettuce plant with a 'Wheelhouse', 'Trailblazer', 'Haymaker', '14RDSJV055-1', '14RDSJV055-3', '14RDSJV055-7', 'PS1102B', 'Hercules', and/or 'Canyon' lettuce plant and seeds derived or produced therefrom.

Objective Description of the Variety 'Wheelhouse'

'Wheelhouse' is an open-pollinated iceberg lettuce variety. This variety is distinct and unique to all other iceberg lettuce varieties due to its earlier maturing time and increased plant weight. Moreover, 'Wheelhouse' has a growing season that includes fall and is adapted to growing in regions such as the Southwest regions of the United States, such as California and the Arizona desert. Lettuce variety 'Wheelhouse' is the result of numerous generations of plant selections chosen for its early maturing time and increased plant weight.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Wheelhouse'.

Lettuce variety 'Wheelhouse' has the following morphologic and other characteristics:
Plant type: Crisp (i.e., iceberg)
Seed:
Color: Black (e.g., comparable to 'Kagraner Sommer')
Leaves:
Shape of cotyledons: Broad
Shape of fourth leaf: Elongated
Apical margin of fourth leaf: Moderately dentate
Basal margin of fourth leaf: Finely dentate
Undulation of fourth leaf: Slight
Green color of fourth leaf: Medium green
Hue of green color of mature outer leaves: Greyish (e.g., comparable to 'Celtuce' and 'Du bon jardinier')
Incision depth of mature leaf: Moderate (e.g., comparable to 'Vanguard')
Indentation of mature leaf: Entire to shallowly dentate
Undulations of the apical margins of mature leaf: Absent/slight to moderate
Anthocyanin coloration: Absent (e.g., comparable to 'Fiorella' and 'Sunrise')
Anthocyanin cupping: Slight
Anthocyanin reflexing: Lateral margins
Anthocyanin size: Large
Anthocyanin glossiness: Moderate (e.g., comparable to 'Salinas')
Anthocyanin blistering: Moderate (e.g., comparable to 'Vanguard')
Anthocyanin leaf thickness: Intermediate
Anthocyanin trichomes: Absent (smooth)
Plant:
Spread of frame leaves: 47.7 cm
Head diameter: 12.6 cm
Head shape: Slightly flattened
Degree of overlapping if upper part of leaves of head: Medium
Head size class: Medium to large
Head per carton: 24
Head weight: 433 g
Plant Butt:
Shape: Flat
Midrib: Flattened (e.g., comparable to 'Salinas')
Plant Core:
Diameter at base of head: 26.6 mm
Core height from base of head to apex: 48.6 mm
Bolting:
Class: Late (e.g., comparable to 'Hilde II')
Height of mature seed stalk: 99.6 cm
Spread of bolter plant: 34 cm
Bolter leaves: Straight
Margin: Dentate
Color: Dark green
Number of days from first water date to seed stalk emergence under summer conditions: 77 days
Bolter Habit:
Terminal inflorescence: Present
Lateral shoots: Present
Basal side shoots: Absent
Disease/Pest Resistance:
Downy Mildew (*Bremia lactucae*) (Bl): Susceptible to Bl:2, Bl:5, Bl:7, Bl:12, Bl:14-Bl:18, Bl:20-Bl:26
Lettuce mosaic virus (LMV) strain Ls-1: Susceptible
Pests:
*Nasonovia ribisnigri* biotype 0 (Nr:0): Susceptible
Comparisons to Commercial Lettuce Variety Table 1 below compares characteristics of lettuce variety 'Wheelhouse' with the lettuce variety 'Gilaben'. Column 1 lists the characteristics, column 2 shows the characteristics for lettuce variety 'Wheelhouse', and column 3 shows the characteristics for lettuce variety 'Gilaben'.

TABLE 1

| Characteristic | 'Wheelhouse' | 'Gilaben' |
| --- | --- | --- |
| Time to maturity | Earlier maturing | Later maturing |
| Plant weight | Increased weight | Lower weight |

Tables 2A and 2B below shows results of a first trial that compares the head weight, head diameter, core length, and frame width of 20 plants of lettuce variety 'Wheelhouse' (Table 2A) with those of 20 plants of lettuce variety 'Gilaben' (Table 2B).

TABLE 2A

| 'Wheelhouse' | Head Wt. | Head Diameter | Core Length | Frame Width |
| --- | --- | --- | --- | --- |
| Max | 745 g | 135 mm | 75 mm | 51 cm |
| Min | 385 g | 115 mm | 45 mm | 44 cm |
| Average | 490.5 g | 126.75 mm | 57 mm | 47.65 cm |
| Std. Dev | 80.13 | 6.13 | 9.23 | 2.30 |

TABLE 2B

| 'Gilaben' | Head Wt. | Head Diameter | Core Length | Frame Width |
| --- | --- | --- | --- | --- |
| Max | 595 g | 145 mm | 85 mm | 51 cm |
| Min | 375 g | 110 mm | 35 mm | 40 cm |
| Average | 472.25 g | 126 mm | 60.5 mm | 47.05 cm |
| Std. Dev | 60.16 | 8.21 | 12.86 | 2.66 |

Tables 3A and 3B below shows results of a second trial that compares the head weight, head diameter, core length, and core diameter of 20 plants of lettuce variety 'Wheelhouse' (Table 3A) with those of 20 plants of lettuce variety 'Gilaben' (Table 3B).

TABLE 3A

| 'Wheelhouse' | Head Wt. | Head Diameter | Core Length | Core Diameter |
| --- | --- | --- | --- | --- |
| Max | 550 g | 135 mm | 65 mm | 32 mm |
| Min | 210 g | 110 mm | 25 mm | 21 mm |
| Average | 375 g | 126.1 mm | 40.2 mm | 26.6 mm |
| Std. Dev | 106.94 | 6.80 | 10.52 | 3.47 |

TABLE 3B

| 'Gilaben' | Head Wt. | Head Diameter | Core Length | Core Diameter |
| --- | --- | --- | --- | --- |
| Max | 465 g | 150 mm | 64 mm | 31 mm |
| Min | 215 g | 111 mm | 20 mm | 20 mm |
| Average | 329.3 g | 128.9 mm | 36.65 mm | 25.65 mm |
| Std. Dev | 77.11 | 10.88 | 12.03 | 2.60 |

Further distinguishing features are apparent from the comparisons of the two varieties 'Wheelhouse' and 'Gilaben' depicted in FIG. 1-5.

Objective Description of the Variety 'Trailblazer'
'Trailblazer' is an open-pollinated romaine lettuce variety. This variety is distinct and unique to all other romaine lettuce varieties due to its later bolting, and darker green color of leaves. Moreover, 'Trailblazer' has a growing season that includes spring and winter, and is adapted to growing in regions in the Southwest, such as California and the Arizona desert, as well as the West Coast regions of the United States. Lettuce variety 'Trailblazer' is the result of numerous generations of plant selections chosen for its late bolting, and dark green color of leaves.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Trailblazer'.

Lettuce variety 'Trailblazer' has the following morphologic and other characteristics:
Plant type: Cos (i.e., romaine)
Seed:
 Color: White (e.g., comparable to 'Verpia')
Leaves:
 Shape of cotyledons: Spatulate
 Shape of fourth leaf: Elongated
 Apical margin of fourth leaf: Entire
 Basal margin of fourth leaf: Finely dentate
 Undulation of fourth leaf: Flat
 Green color of fourth leaf: Yellow-green
 Hue of green color of outer leaves: Yellowish (e.g., comparable to 'Dorée de printemps')
 Incision depth of mature leaf: Moderate (e.g., comparable to 'Vanguard')
 Indentation of mature leaf: Shallowly dentate (e.g., comparable to 'Great Lakes 65')
 Undulations of the apical margins of mature leaf: Absent/slight (e.g., comparable to 'Dark Green Boston')
 Anthocyanin coloration: Absent
 Anthocyanin cupping: Slight
 Anthocyanin reflexing: Apical margin
 Anthocyanin size: Medium
 Anthocyanin glossiness: Moderate (e.g., comparable to 'Salinas')
 Anthocyanin blistering: Moderate (e.g., comparable to 'Vanguard')
 Anthocyanin leaf thickness: Intermediate
 Anthocyanin trichomes: Absent (smooth)
Plant:
 Spread of frame leaves: 48.1 cm
 Head shape: Elongate
 Head size class: Large
 Head per carton: 24
 Head weight: 607.5 g
 Head firmness: Firm
Plant Butt:
 Shape: Rounded
 Midrib: Moderately raised
Plant Core:
 Core height from base to head to apex: 69.3 mm
Bolting:
 Class: Early (e.g., comparable to 'Gotte à graine blanche')
 Height of mature seed stalk: 96.4 cm
 Spread of bolter plant: 34 cm
 Bolter leaves: Straight
 Margin: Entire
 Color: Light green
 Number of days from first water date to seed stalk emergence under summer conditions: 67 days Bolter Habit:
 Terminal inflorescence: Absent
 Lateral shoots: Absent
 Basal side shoots: Present
Disease/Pest Resistance:
 Downy Mildew (*Bremia lactucae*) (Bl): Susceptible to Bl:2, Bl:5, Bl:7, Bl:12, Bl:14-Bl:18, Bl:20-Bl:26
 Lettuce mosaic virus (LMV) strain Ls-1: Susceptible
Pests:
 *Nasonovia ribisnigri* biotype 0 (Nr:0): Susceptible
Comparisons to Commercial Lettuce Variety Table 4A below compares characteristics of lettuce variety 'Trailblazer' with the lettuce variety 'Mammoth'. Column 1 lists the characteristics, column 2 shows the characteristics for lettuce variety 'Trailblazer', and column 3 shows the characteristics for lettuce variety 'Mammoth'

TABLE 4A

| Characteristic | 'Trailblazer' | 'Mammoth' |
| --- | --- | --- |
| Bolting | Early | Earlier bolting |
| Color of leaves | Darker green color | Lighter green color |

Tables 4B and 4C below shows results of a trial that compares the heart weight, heart length, core length, and core diameter of 20 plants of lettuce variety 'Trailblazer' (Table 4B) with those of 20 plants of lettuce variety 'Mammoth' (Table 4C).

TABLE 4B

| 'Trailblazer' | Heart Wt. | Heart Length | Core Length | Core Diameter |
| --- | --- | --- | --- | --- |
| Max | 795 g | 380 mm | 92 mm | 40 mm |
| Min | 485 g | 240 mm | 46 mm | 28 mm |
| Average | 607.5 g | 316.5 mm | 69.3 mm | 34.85 mm |
| Std. Dev | 90.36 | 39.41 | 10.46 | 3.41 |

TABLE 4C

| 'Mammoth' | Heart Wt. | Heart Length | Core Length | Core Diameter |
| --- | --- | --- | --- | --- |
| Max | 890 g | 380 mm | 86 mm | 39 mm |
| Min | 375 g | 320 mm | 55 mm | 26 mm |
| Average | 559.25 g | 343.5 mm | 69.65 mm | 33.1 mm |
| Std. Dev | 116.53 | 16.23 | 9.74 | 3.14 |

Further distinguishing features are apparent from the comparisons of the two varieties 'Trailblazer' and 'Mammoth' depicted in FIG. 6-9.

Objective Description of the Variety 'Haymaker'

'Haymaker' is an open-pollinated iceberg lettuce variety. This variety is distinct and unique to other iceberg lettuce varieties due to its improved uniformity, stronger heading, improved tolerance to tip burn, and increased weight. Moreover, 'Haymaker' has a growing season that includes summer and winter, and is adapted to growing in regions in the Southwest, such as California and the Arizona desert, as well as the West Coast regions of the United States. Lettuce variety 'Haymaker' is the result of numerous generations of plant selections chosen for its improved uniformity, stronger heading, improved tolerance to tip burn, and increased weight.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Haymaker'.

Lettuce variety 'Haymaker' has the following morphologic and other characteristics:
Plant type: Crisp (i.e., iceberg)
Seed:
Color: Black (e.g., comparable to 'Kagraner Sommer')
Leaves:
Shape of cotyledons: Broad
Shape of fourth leaf: Oval
Apical margin of fourth leaf: Crenate/gnawed
Basal margin of fourth leaf: Moderately dentate
Undulation of fourth leaf: Flat
Green color of fourth leaf: Dark green
Hue of green color of outer leaves: Greyish (e.g., comparable to 'Celtuce' and 'Du bon jardinier')
Incision depth of mature leaf: Moderate (e.g., comparable to 'Vanguard')
Indentation of mature leaf: Deeply dentate (e.g., comparable to 'Great Lakes 659')
Undulations of the apical margins of mature leaf: Strong (e.g., comparable to 'Great Lakes 659')
Anthocyanin coloration: Absent (e.g., comparable to 'Fiorella' and 'Sunrise')
Anthocyanin cupping: Uncupped
Anthocyanin reflexing: None
Anthocyanin concentration: Moderate (e.g., comparable to 'Prize Head')
Anthocyanin size: Medium
Anthocyanin blistering: Moderate (e.g., comparable to 'Vanguard')
Anthocyanin leaf thickness: Intermediate
Anthocyanin trichomes: Absent (smooth)
Plant:
Spread of frame leaves: 49.8 cm
Head diameter: 135.3 mm
Head shape: Slightly flattened
Degree of overlapping if upper part of leaves of head: Strong
Head size class: Medium
Head per carton: 24
Head weight: 680.53 g
Head firmness: Firm
Plant Butt:
Shape: Rounded
Midrib: Moderately raised
Plant Core:
Diameter at base of head: 31.1 mm
Core height from base to head to apex: 44.25 mm
Bolting:
Class: Medium (e.g., comparable to 'Carelia')
Height of mature seed stalk: 96 cm
Spread of bolter plant: 38.2 cm
Bolter leaves: Curved
Margin: Dentate
Color: Dark green
Number of days from first water date to seed stalk emergence under summer conditions: 59 days
Bolter Habit:
Terminal inflorescence: Present
Lateral shoots: Present
Basal side shoots: Present
Disease/Pest Resistance:
Downy Mildew (*Bremia lactucae*) (Bl): Susceptible to Bl:2, Bl:5, Bl:7, Bl:12, Bl:14-Bl:18, Bl:20-Bl:26

Lettuce mosaic virus (LMV) strain Ls-1: Susceptible
Pests:
*Nasonovia ribisnigri* biotype 0 (Nr:0): Susceptible
Comparisons to Commercial Lettuce Variety Table 5 below compares characteristics of lettuce variety 'Haymaker' with the lettuce variety 'Venus'. Column 1 lists the characteristics, column 2 shows the characteristics for lettuce variety 'Haymaker', and column 3 shows the characteristics for lettuce variety 'Venus'.

TABLE 5

| Characteristic | 'Haymaker' | 'Venus' |
| --- | --- | --- |
| Uniformity | Improved uniformity | Uniform |
| Heading | Stronger heading | Weaker heading |
| Tip burn tolerance | Improved tolerance | Tolerant |
| Plant weight | Comparable weight | Comparable weight |

Tables 6A and 6B below shows results of a first trial that compares the head weight, head circumference, core length, and core diameter of 20 plants of lettuce variety 'Haymaker' (Table 6A) with those of 20 plants of lettuce variety 'Venus' (Table 6B).

TABLE 6A

| 'Haymaker' | Head Wt. | Head Circumference | Core Length | Core Diameter |
| --- | --- | --- | --- | --- |
| Max | 865 g | 490 mm | 50 mm | 39 mm |
| Min | 495 g | 425 mm | 22 mm | 28 mm |
| Average | 712.75 g | 459.05 mm | 37.35 mm | 31.75 mm |
| Std. Dev | 92.34 | 21.13 | 8.05 | 3.13 |

TABLE 6B

| 'Venus' | Head Wt. | Head Circumference | Core Length | Core Diameter |
| --- | --- | --- | --- | --- |
| Max | 805 g | 470 mm | 51 mm | 38 mm |
| Min | 595 g | 429 mm | 25 mm | 28 mm |
| Average | 671.8 g | 447.1 mm | 40.45 mm | 32.6 mm |
| Std. Dev | 65.06 | 12.59 | 7.24 | 2.56 |

Tables 7A and 7B below shows results of a second trial that compares the head weight, head diameter, core length, and frame width of 20 plants of lettuce variety 'Haymaker' (Table 7A) with those of 20 plants of lettuce variety 'Venus' (Table 7B).

TABLE 7A

| 'Haymaker' | Head Wt. | Head Diameter | Core Length | Frame Width |
| --- | --- | --- | --- | --- |
| Max | 875 g | 165 mm | 50 mm | 52 cm |
| Min | 385 g | 125 mm | 25 mm | 46 cm |
| Average | 635.6 g | 142 mm | 38.5 mm | 48.95 cm |
| Std. Dev | 145.28 | 10.81 | 6.09 | 2.14 |

TABLE 7B

| 'Venus' | Head Wt. | Head Diameter | Core Length | Frame Width |
| --- | --- | --- | --- | --- |
| Max | 860 g | 165 mm | 50 mm | 54 cm |
| Min | 450 g | 110 mm | 30 mm | 43 cm |
| Average | 646 g | 142.25 mm | 40 mm | 48.25 cm |
| Std. Dev | 102.95 | 13.13 | 5.13 | 3.46 |

Tables 8A and 8B below shows results of a third trial that compares the head weight, head diameter, core length, core diameter, and frame width of 20 plants of lettuce variety 'Haymaker' (Table 8A) with those of 20 plants of lettuce variety 'Venus' (Table 8B).

TABLE 8A

| 'Haymaker' | Head Wt. | Head Diameter | Core Length | Core Diameter | Frame Width |
|---|---|---|---|---|---|
| Max | 835 g | 145 mm | 75 mm | 34 mm | 58 cm |
| Min | 585 g | 120 mm | 23 mm | 27 mm | 45 cm |
| Average | 693.25 g | 128.6 mm | 49.95 mm | 31.1 mm | 50.65 cm |
| Std. Dev | 72.65 | 6.81 | 13.33 | 1.41 | 4.49 |

TABLE 8B

| 'Venus' | Head Wt. | Head Diameter | Core Length | Core Diameter | Frame Width |
|---|---|---|---|---|---|
| Max | 835 g | 145 mm | 73 mm | 34 mm | 56 cm |
| Min | 515 g | 116 mm | 25 mm | 25 mm | 43 cm |
| Average | 723.5 g | 129.2 mm | 47 mm | 30.8 mm | 49.2 cm |
| Std. Dev | 83.07 | 8.11 | 15.52 | 2.17 | 3.32 |

Figure 11A:
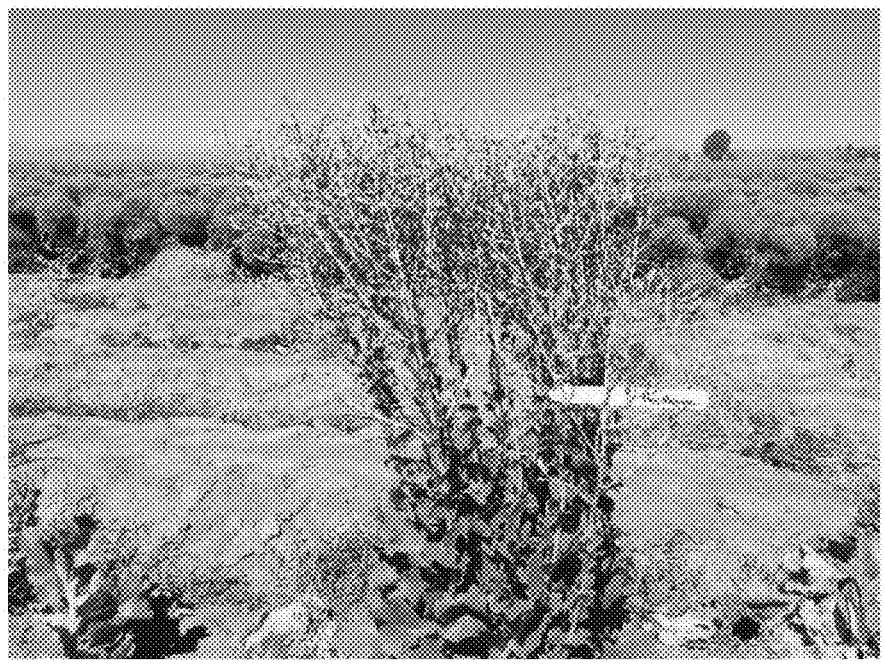
FIGS. 11A and 11B show a comparison between lettuce varieties 'Haymaker' and 'Venus'.
Figure 11B:
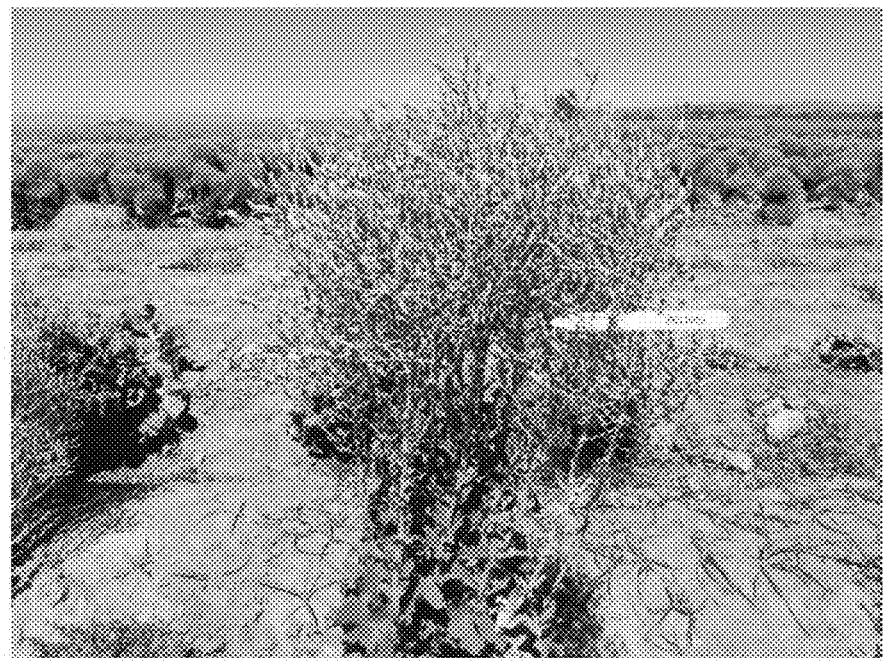
Figure 12A:
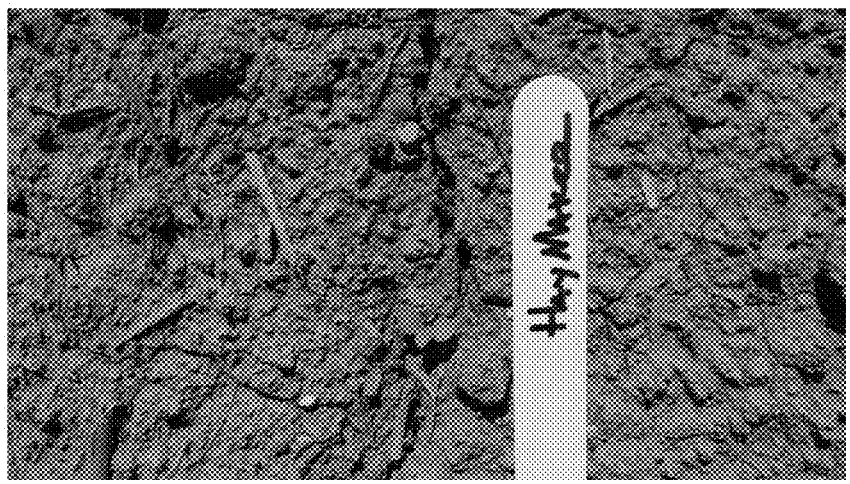
FIGS. 12A, 12B, and 12C show a comparison between lettuce varieties 'Haymaker' and 'Venus'.
Figure 12B:
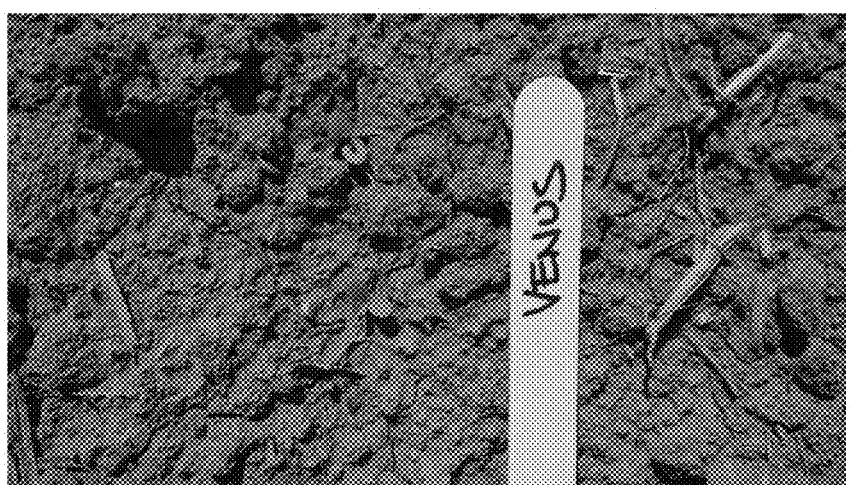
Figure 12C:
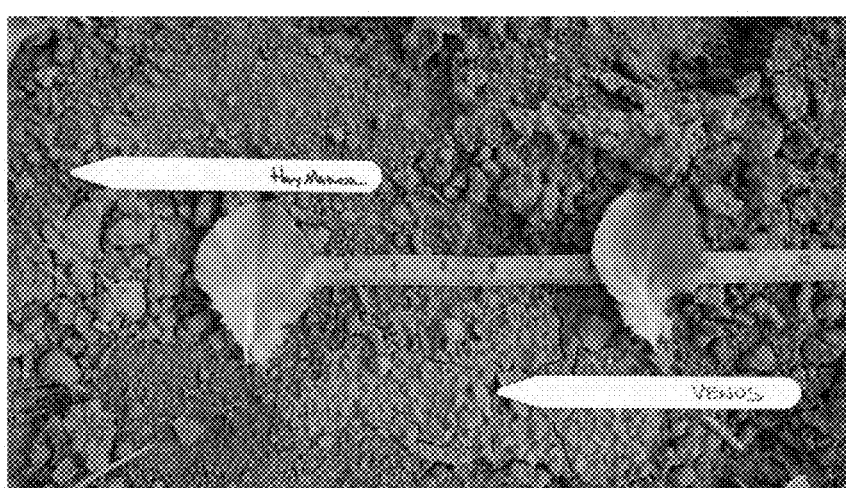
Figure 13A:
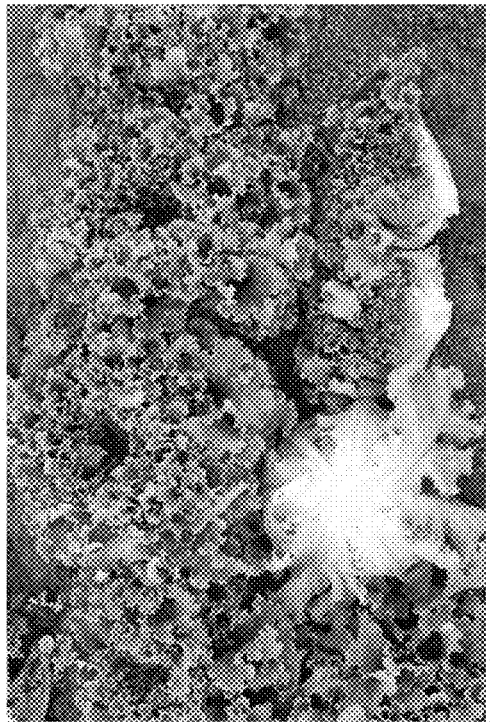
FIGS. 13A, 13B, 13C, and 13D show a comparison between lettuce varieties '14RDSJV055-1', '14RDSJV055-3', '14RDSJV055-7' and 'Oso Verde'.
Figure 13B:
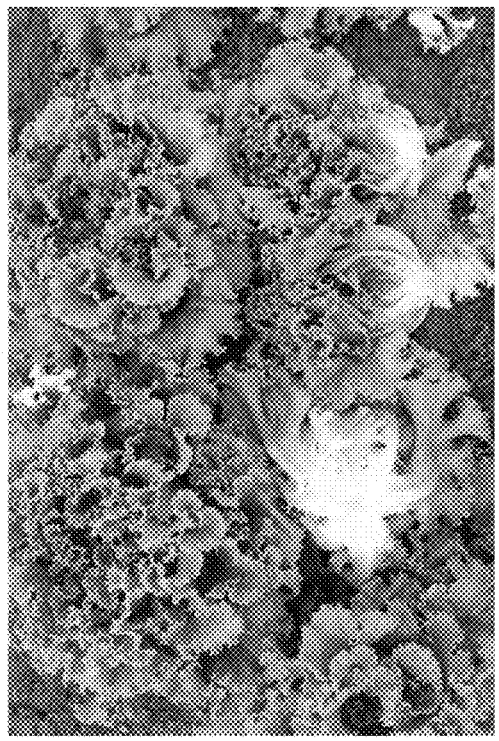
Figure 13C:
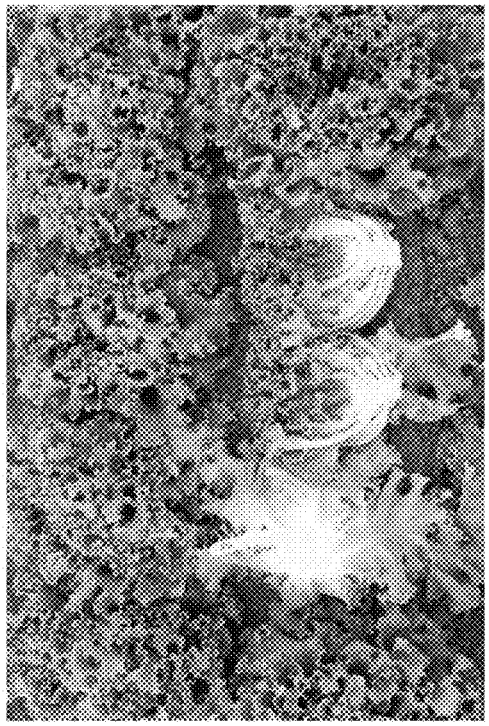
Figure 13D:
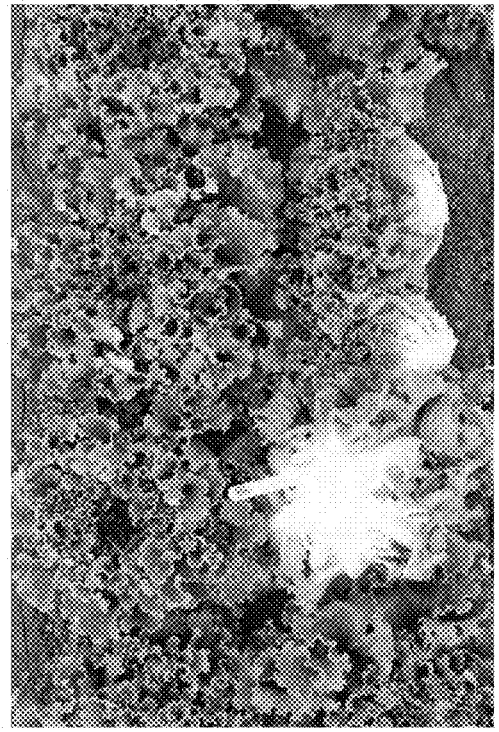
Figure 14A:
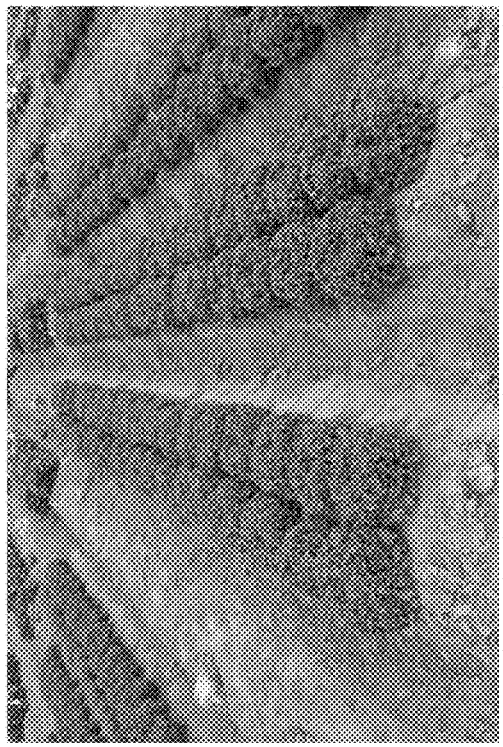
FIGS. 14A, 14B, 14C, and 14D show a comparison between lettuce varieties '14RDSJV055-1', '14RDSJV055-3', '14RDSJV055-7' and 'Oso Verde'.
Figure 14B:
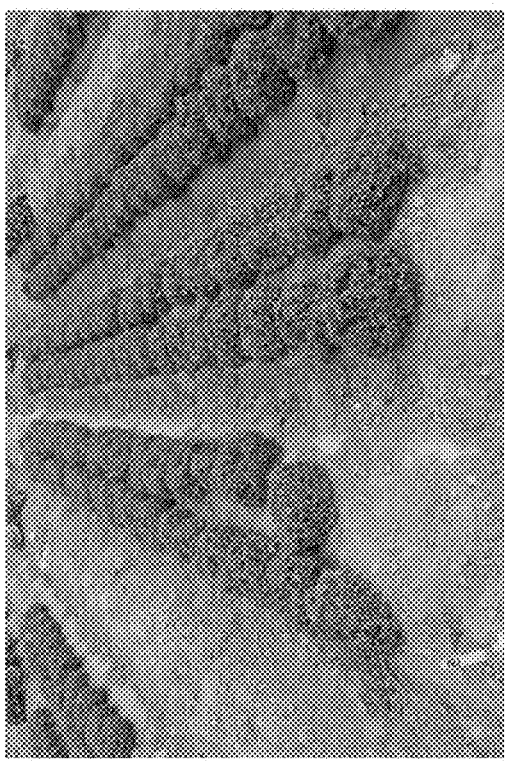
Figure 14C:
Figure 14D:
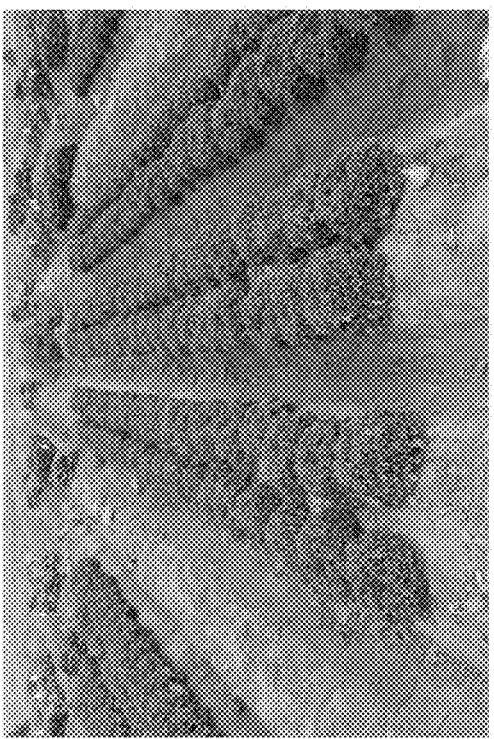
Figure 15A:
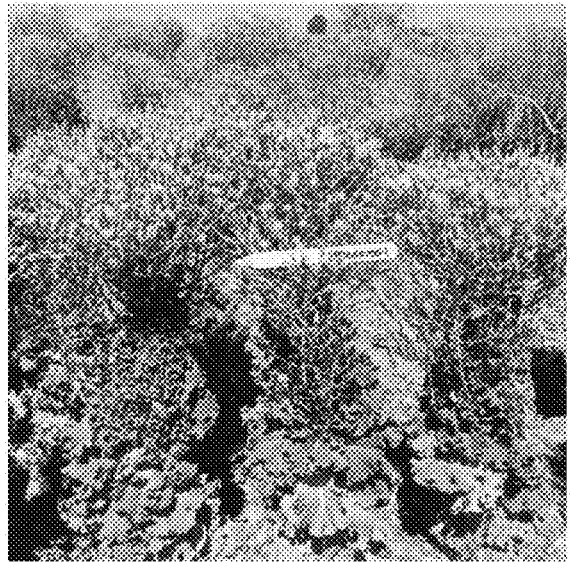
FIGS. 15A, 15B, 15C, and 15D show a comparison between lettuce varieties '14RDSJV055-1', '14RDSJV055-3', '14RDSJV055-7' and 'Oso Verde'.
Figure 15B:
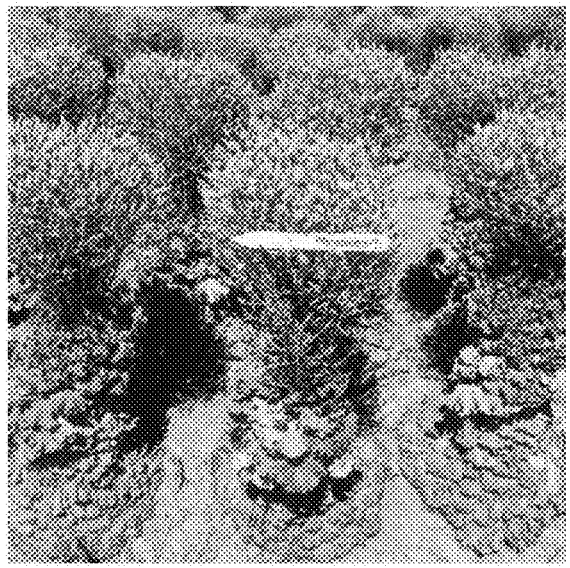
Figure 15C:
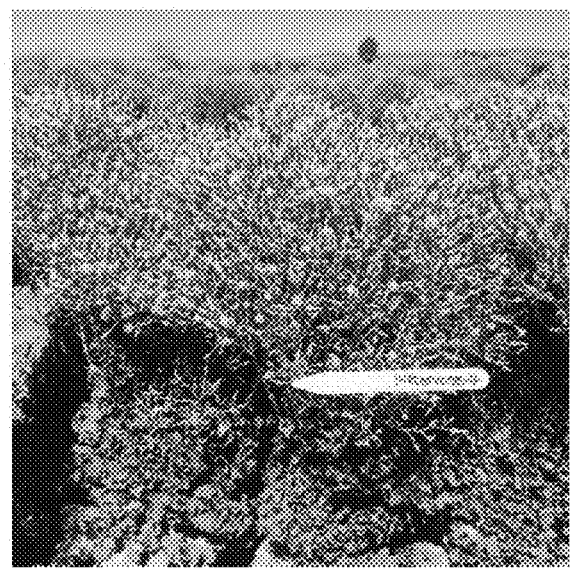
Figure 15D:
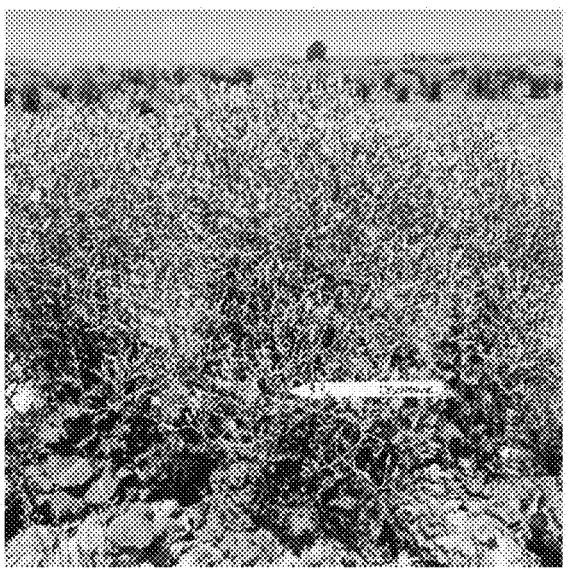
Figure 16A:
FIGS. 16A, 16B, 16C, and 16D show a comparison between lettuce varieties '14RDSJV055-1', '14RDSJV055-3', '14RDSJV055-7' and 'Oso Verde'.
Figure 16B:
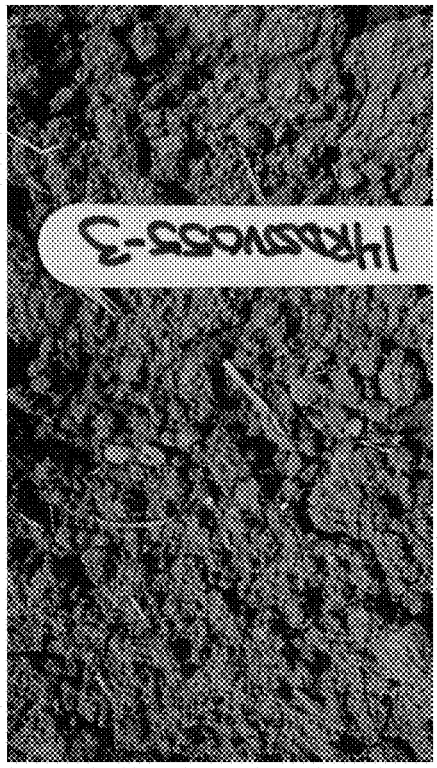
Figure 16C:
Figure 16D:
Figure 17A:
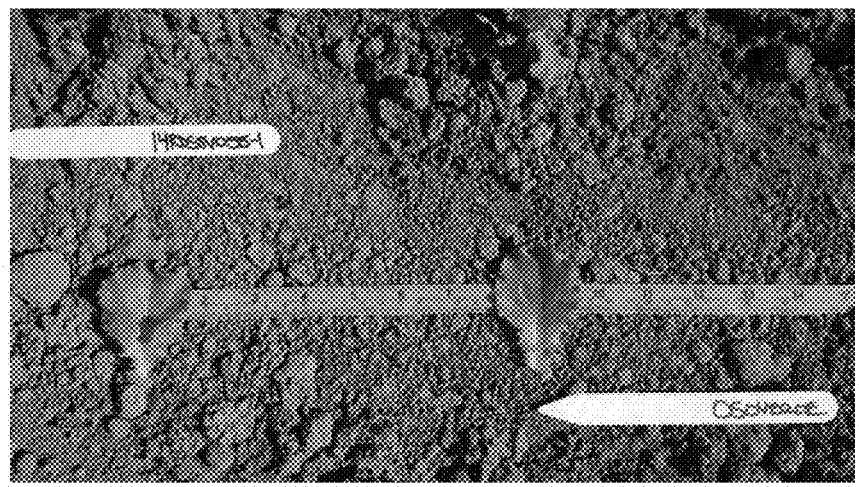
FIG. 17A shows a comparison of leaflets of lettuce varieties '14RDSJV055-1' and 'Oso Verde'.
Figure 17B:
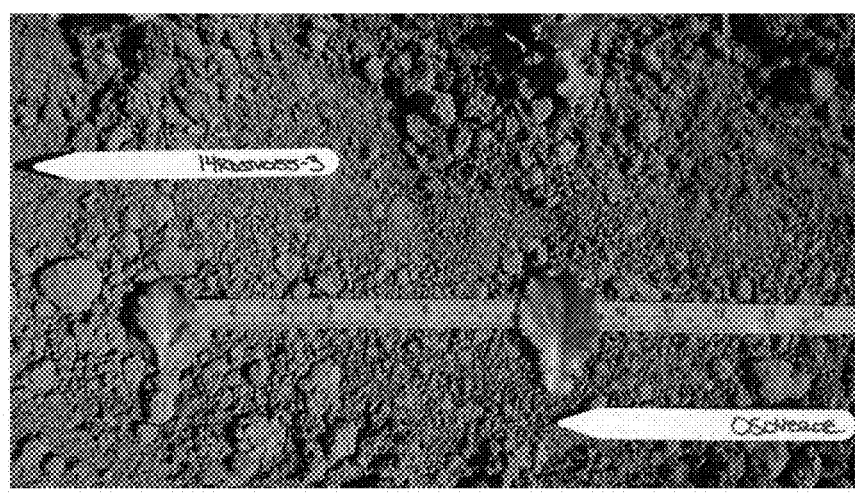
FIG. 17B shows a comparison of leaflets of lettuce varieties '14RDSJV055-3' and 'Oso Verde'.
Figure 17C:
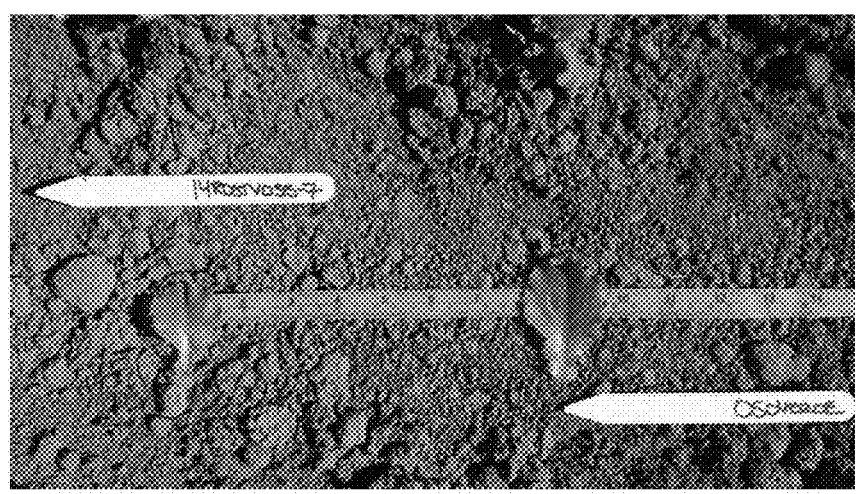
FIG. 17C shows a comparison of leaflets of lettuce varieties '14RDSJV055-7' and 'Oso Verde'.
Figure 18A:
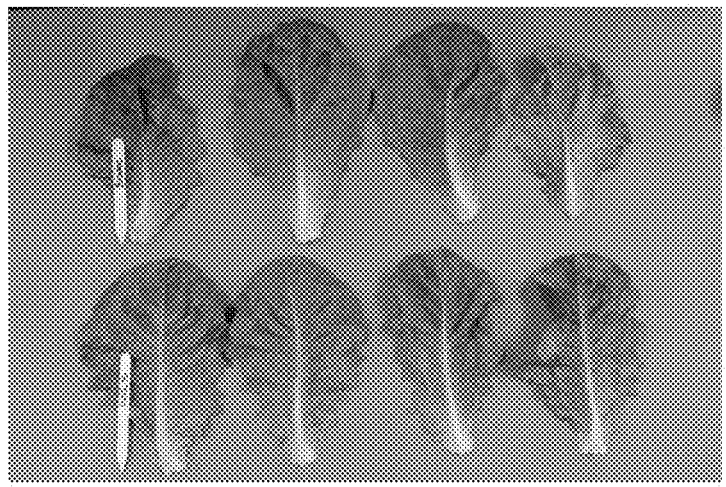
FIGS. 18A, 18B, 18C, 18D, and 18E show a comparison between lettuce varieties 'PS1102B' and 'Bondi'.
Figure 18B:
Figure 18C:
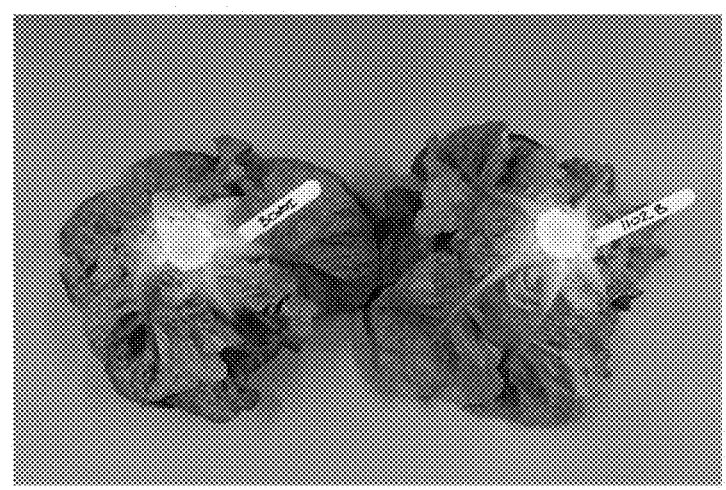
Figure 18D:
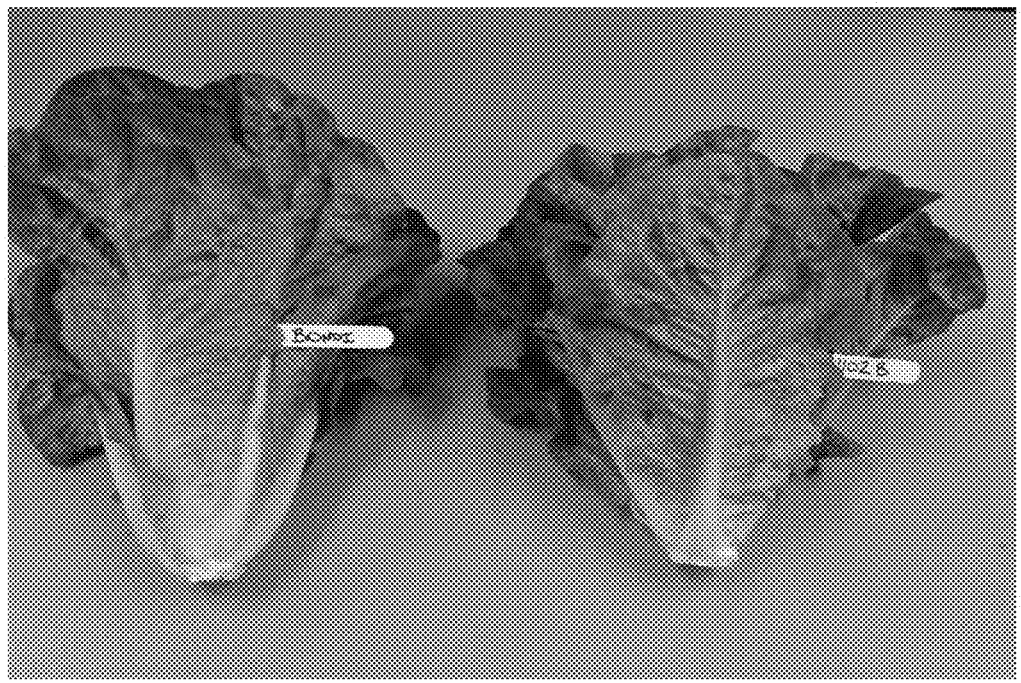
Figure 18E:

Further distinguishing features are apparent from the comparisons of the two varieties 'Haymaker' and 'Venus' depicted in FIG. 10-12.

Objective Description of the Variety '14RDSJV055-1'

'14RDSJV055-1' is an open-pollinated cutting (i.e., looseleaf) lettuce variety. This variety is distinct and unique to all other cutting lettuce varieties due to its thicker texture, darker leaf color, compact frame, rounder leaf shape, and later bolting. Lettuce variety '14RDSJV055-1' is the result of numerous generations of plant selections chosen for its thick texture, dark leaf color, compact frame, round leaf shape, and late bolting.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '14RDSJV055-1'.

Lettuce variety '14RDSJV055-1' has the following morphologic and other characteristics:

Plant type: Cutting (e.g., comparable to 'Frisée d'Amérique', 'Lollo rossa', 'Oakleaf', and 'Salad Bowl')

Seed:

Color: Black (e.g., comparable to 'Kagraner Sommer')

Leaves:

Hue of green color of outer leaves: Greyish (e.g., comparable to 'Celtuce' and 'Du bon jardinier')

Anthocyanin coloration: Absent (e.g., comparable to 'Fiorella' and 'Sunrise')

Bolting:

Class: Late (e.g., comparable to 'Hilde II')

Disease/Pest Resistance:

Downy Mildew (*Bremia lactucae*) (Bl): Susceptible to Bl:2, Bl:5, Bl:7, Bl:12, Bl:14-Bl:18, Bl:20-Bl:26

Lettuce mosaic virus (LMV) strain Ls-1: Susceptible

Pests:

*Nasonovia ribisnigri* biotype 0 (Nr:0): Susceptible

Comparisons to Commercial Lettuce Variety

Table 9 below compares characteristics of lettuce variety '14RDSJV055-1' with the lettuce variety 'Oso Verde'. Column 1 lists the characteristics, column 2 shows the characteristics for lettuce variety '14RDSJV055-1', and column 3 shows the characteristics for lettuce variety 'Oso Verde'.

TABLE 9

| Characteristic | '14RDSJV055-1' | 'Oso Verde' |
|---|---|---|
| Texture | Thicker | Less thick |
| Leaf color | Darker color | Lighter color |
| Frame | Compact frame | Less compact frame |
| Leaf shape | Rounder leaf | Less round leaf |
| Bolting | Later bolting | Earlier bolting |

Tables 10A and 10B below shows results of a trial that compares the heart weight, heart length, and core length of five plants of lettuce variety '14RDSJV055-1' (Table 10A) with those of five plants of lettuce variety 'Oso Verde' (Table 10B).

TABLE 10A

| '14RDSJV055-1' | Heart Wt. | Heart Length | Core Length |
|---|---|---|---|
| Max | 450 g | 165 mm | 43 mm |
| Min | 280 g | 152 mm | 31 mm |
| Average | 364 g | 155 mm | 37.4 mm |
| Std. Dev | 63.58 | 5.61 | 4.28 |

TABLE 10B

| 'Oso Verde' | Heart Wt. | Heart Length | Core Length |
|---|---|---|---|
| Max | 580 g | 279 mm | 38 mm |
| Min | 415 g | 235 mm | 32 mm |
| Average | 469 g | 257.8 mm | 34.4 mm |
| Std. Dev | 66.56 | 16.45 | 2.88 |

Further distinguishing features are apparent from the comparisons of the varieties '14RDSJV055-1', '14RDSJV055-3', '14RDSJV055-7', and 'Oso Verde' depicted in FIG. 13-17.

Objective Description of the Variety '14RDSJV055-3'

'14RDSJV055-3' is an open-pollinated cutting (i.e., looseleaf) lettuce variety. This variety is distinct and unique to all other cutting lettuce varieties due to its thicker texture, darker leaf color, compact frame, rounder leaf shape, and later bolting. Lettuce variety '14RDSJV055-3' is the result of numerous generations of plant selections chosen for its thick texture, dark leaf color, compact frame, round leaf shape, and late bolting. Lettuce variety '14RDSJV055-3' is distinguished from '14RDSJV055-1' in that '14RDSJV055-3' has improved uniformity as compared to '14RDSJV055-1'.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '14RDSJV055-3'.

Lettuce variety '14RDSJV055-3' has the following morphologic and other characteristics:

Plant type: Cutting (e.g., comparable to 'Frisée d'Amérique', 'Lollo rossa', 'Oakleaf', and 'Salad Bowl')

Seed:
Color: Black (e.g., comparable to 'Kagraner Sommer')

Leaves:
Hue of green color of outer leaves: Greyish (e.g., comparable to 'Celtuce' and 'Du bon jardinier')
Anthocyanin coloration: Absent (e.g., comparable to 'Fiorella' and 'Sunrise')

Bolting:
Class: Late (e.g., comparable to 'Hilde II')

Disease/Pest Resistance:
Downy Mildew (*Bremia lactucae*) (Bl): Susceptible to Bl:2, Bl:5, Bl:7, Bl:12, Bl:14-Bl:18, Bl:20-Bl:26
Lettuce mosaic virus (LMV) strain Ls-1: Susceptible Pests:
*Nasonovia ribisnigri* biotype 0 (Nr:0): Susceptible Comparisons to Commercial Lettuce Variety Table 11 below compares characteristics of lettuce variety '14RDSJV055-3' with the lettuce variety 'Oso Verde'. Column 1 lists the characteristics, column 2 shows the characteristics for lettuce variety '14RDSJV055-3', and column 3 shows the characteristics for lettuce variety 'Oso Verde'.

TABLE 11

| Characteristic | '14RDSJV055-3' | 'Oso Verde' |
| --- | --- | --- |
| Texture | Thicker | Less thick |
| Leaf color | Darker color | Lighter color |
| Frame | Compact frame | Less compact frame |
| Leaf shape | Rounder leaf | Less round leaf |
| Bolting | Later bolting | Earlier bolting |

Tables 12A and 12B below shows results of a trial that compares the heart weight, heart length, and core length of five plants of lettuce variety '14RDSJV055-3' (Table 12A) with those of five plants of lettuce variety 'Oso Verde' (Table 12B).

TABLE 12A

| '14RDSJV055-3' | Heart Wt. | Heart Length | Core Length |
| --- | --- | --- | --- |
| Max | 370 g | 171 mm | 44 mm |
| Min | 285 g | 153 mm | 37 mm |
| Average | 309 g | 164.6 mm | 41.2 mm |
| Std. Dev | 35.25 | 6.80 | 3.42 |

TABLE 12B

| 'Oso Verde' | Heart Wt. | Heart Length | Core Length |
| --- | --- | --- | --- |
| Max | 580 g | 279 mm | 38 mm |
| Min | 415 g | 235 mm | 32 mm |
| Average | 469 g | 257.8 mm | 34.4 mm |
| Std. Dev | 66.56 | 16.45 | 2.88 |

Further distinguishing features are apparent from the comparisons of the varieties '14RDSJV055-3', '14RDSJV055-1', '14RDSJV055-7', and 'Oso Verde' depicted in FIG. 13-17.

Objective Description of the Variety '14RDSJV055-7'

'14RDSJV055-7' is an open-pollinated cutting (i.e., looseleaf) lettuce variety. This variety is distinct and unique to all other cutting lettuce varieties due to its thicker texture, darker leaf color, compact frame, rounder leaf shape, and later bolting. Lettuce variety '14RDSJV055-7' is the result of numerous generations of plant selections chosen for its thick texture, dark leaf color, compact frame, round leaf shape, and late bolting. Lettuce variety '14RDSJV055-3' is the result of numerous generations of plant selections chosen for its thick texture, dark leaf color, compact frame, round leaf shape, and late bolting. Lettuce variety '14RDSJV055-7' is distinguished from '14RDSJV055-1' and '14RDSJV055-3' in that '14RDSJV055-7' is earlier bolting to '14RDSJV055-3' and over '4RDSJV055-1'; and is larger in size as compared to '14RDSJV055-1' and '14RDSJV055-3'.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety '14RDSJV055-7'.

Lettuce variety '14RDSJV055-7' has the following morphologic and other characteristics:

Plant type: Cutting (e.g., comparable to 'Frisée d'Amérique', 'Lollo rossa', 'Oakleaf', and 'Salad Bowl')

Seed:
Color: Black (e.g., comparable to 'Kagraner Sommer')

Leaves:
Hue of green color of outer leaves: Greyish (e.g., comparable to 'Celtuce' and 'Du bon jardinier')
Anthocyanin coloration: Absent (e.g., comparable to 'Fiorella' and 'Sunrise')

Bolting:
Class: Late (e.g., comparable to 'Hilde II')

Disease/Pest Resistance:
Downy Mildew (*Bremia lactucae*) (Bl): Susceptible to Bl:2, Bl:5, Bl:7, Bl:12, Bl:14-Bl:18, Bl:20-Bl:26
Lettuce mosaic virus (LMV) strain Ls-1: Susceptible Pests:
*Nasonovia ribisnigri* biotype 0 (Nr:0): Susceptible Comparisons to Commercial Lettuce Variety Table 13 below compares characteristics of lettuce variety '14RDSJV055-7' with the lettuce variety 'Oso Verde'. Column 1 lists the characteristics, column 2 shows the characteristics for lettuce variety '14RDSJV055-7', and column 3 shows the characteristics for lettuce variety 'Oso Verde'.

TABLE 13

| Characteristic | '14RDSJV055-7' | 'Oso Verde' |
| --- | --- | --- |
| Texture | Thicker | Less thick |
| Leaf color | Darker color | Lighter color |
| Frame | Compact frame | Less compact frame |
| Leaf shape | Rounder leaf | Less round leaf |
| Bolting | Later bolting | Earlier bolting |

Tables 14A and 14B below shows results of a trial that compares the heart weight, heart length, and core length of five plants of lettuce variety '14RDSJV055-7' (Table 14A) with those of five plants of lettuce variety 'Oso Verde' (Table 14B).

TABLE 14A

| '14RDSJV055-7' | Heart Wt. | Heart Length | Core Length |
|---|---|---|---|
| Max | 300 g | 153 mm | 38 mm |
| Min | 250 g | 133 mm | 32 mm |
| Average | 274 g | 146.2 mm | 35.4 mm |
| Std. Dev | 21.03 | 7.98 | 3.13 |

TABLE 14B

| 'Oso Verde' | Heart Wt. | Heart Length | Core Length |
|---|---|---|---|
| Max | 580 g | 279 mm | 38 mm |
| Min | 415 g | 235 mm | 32 mm |
| Average | 469 g | 257.8 mm | 34.4 mm |
| Std. Dev | 66.56 | 16.45 | 2.88 |

Further distinguishing features are apparent from the comparisons of the varieties '14RDSJV055-7', '14RDSJV055-1', '14RDSJV055-3', and 'Oso Verde' depicted in FIG. 13-17.

Objective Description of the Variety 'PS1102B'

'PS1102B' is an open-pollinated romaine lettuce variety. This variety is distinct and unique to all other romaine lettuce varieties due to its earlier bolting, improved uniformity, improved texture, earlier cupping, increased plant weight, and darker green leaf color. Lettuce variety 'PS1102B' is the result of numerous generations of plant selections chosen for its earlier bolting, improved uniformity, improved texture, earlier cupping, increased plant weight, and darker green leaf color.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'PS1102B'.

Lettuce variety 'PS1102B' has the following morphologic and other characteristics:

Plant type: Cos (i.e., romaine)
Seed:
Color: White (e.g., comparable to 'Verpia')
Leaves:
Hue of green color of outer leaves: Greyish (e.g., comparable to 'Celtuce' and 'Du bon jardinier')
Anthocyanin coloration: Absent (e.g., comparable to 'Fiorella' and 'Sunrise')
Bolting:
Class: Early (e.g., comparable to 'Gotte á graine blanche')
Disease/Pest Resistance:
Downy Mildew (*Bremia lactucae*) (Bl): Susceptible to Bl:2, Bl:5, Bl:7, Bl:12, Bl:14-Bl:18, Bl:20-Bl:26
Lettuce mosaic virus (LMV) strain Ls-1: Susceptible
Pests:
*Nasonovia ribisnigri* biotype 0 (Nr:0): Susceptible Comparisons to Commercial Lettuce Variety Table 15 below compares characteristics of lettuce variety 'PS1102B' with the lettuce variety 'Bondi'. Column 1 lists the characteristics, column 2 shows the characteristics for lettuce variety 'PS1102B', and column 3 shows the characteristics for lettuce variety 'Bondi'.

TABLE 15

| Characteristic | 'PS1102B' | 'Bondi' |
|---|---|---|
| Bolting | Earlier bolting | Later bolting |
| Uniformity | Improved uniformity | Uniform |
| Texture | Improved texture | Good texture |
| Cupping | Earlier cupping | Later cupping |
| Plant weight | Increased weight | Lower weight |
| Leaf color | Darker green color | Lighter green color |

Tables 16A and 16B below shows results of a trial that compares the heart weight, heart length, core length, and core diameter of 20 plants of lettuce variety 'PS1102B' (Table 16A) with those of 20 plants of lettuce variety 'Bondi' (Table 16B).

TABLE 16A

| 'PS1102B' | Heart Wt. | Heart Length | Core Length | Core Diameter |
|---|---|---|---|---|
| Max | 1100 g | 360 mm | 100 mm | 47 mm |
| Min | 585 g | 280 mm | 45 mm | 31 mm |
| Average | 786.25 g | 302.75 mm | 73.05 mm | 43.2 mm |
| Std. Dev | 140.36 | 22.68 | 15.31 | 3.95 |

TABLE 16B

| 'Bondi' | Heart Wt. | Heart Length | Core Length | Core Diameter |
|---|---|---|---|---|
| Max | 805 g | 350 mm | 110 mm | 46 mm |
| Min | 425 g | 270 mm | 45 mm | 32 mm |
| Average | 570.75 g | 316 mm | 72 mm | 39.95 mm |
| Std. Dev | 110.06 | 19.17 | 18.38 | 4.39 |

Figure 19A:
FIGS. 19A and 19B show a comparison between lettuce varieties 'PS1102B' and 'Bondi'.
Figure 19B:
Figure 20A:
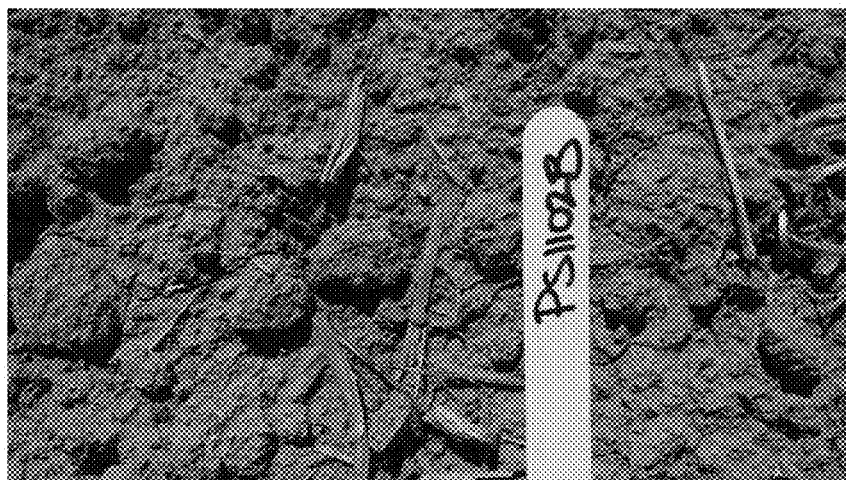
FIGS. 20A, 20B, and 20C show a comparison between lettuce varieties 'PS1102B' and 'Bondi'.
Figure 20B:
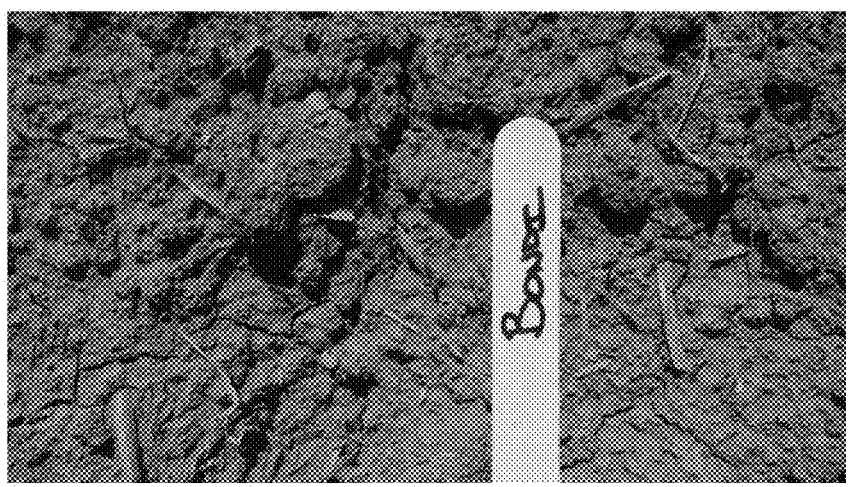
Figure 20C:
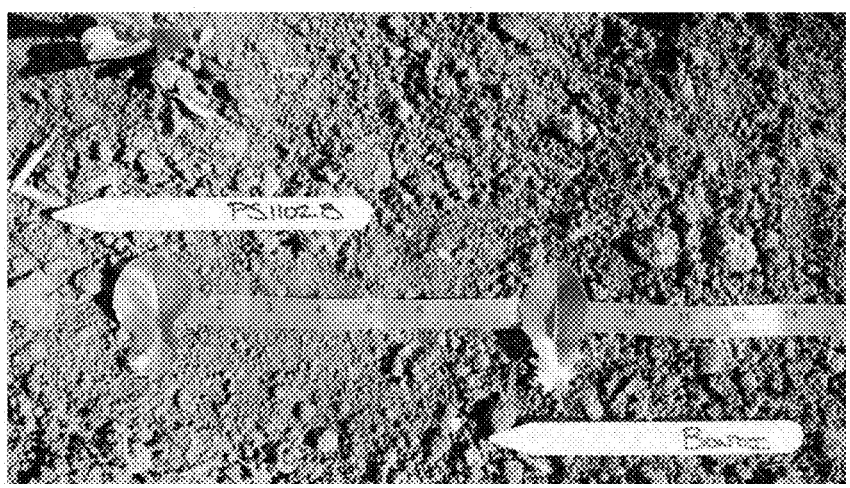
Figure 21A:
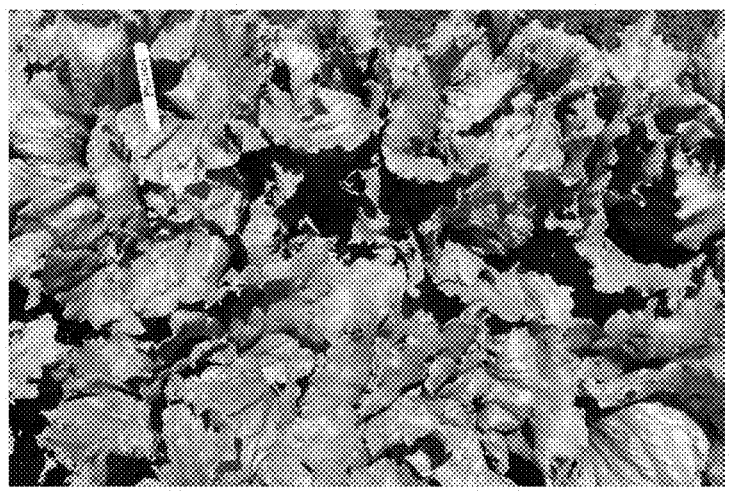
FIGS. 21A, 21B, and 21C show a comparison between lettuce varieties 'Canyon', 'Hercules', and 'Regency'.
Figure 21B:
Figure 21C:
Figure 22A:
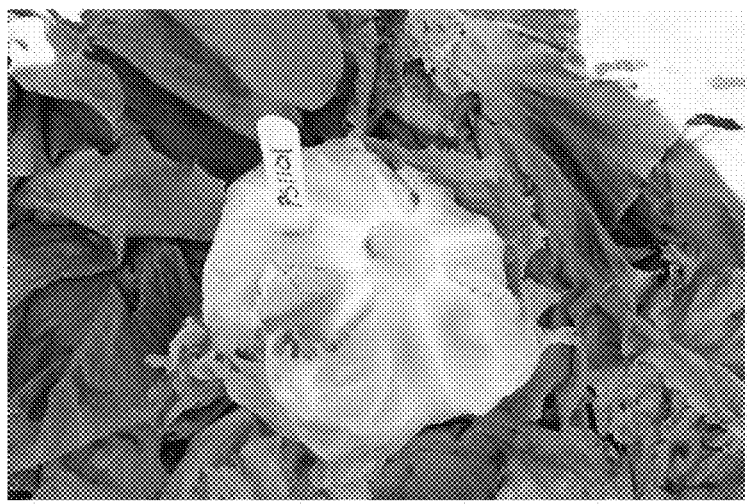
FIGS. 22A, 22B, and 22C show a comparison between lettuce varieties 'Canyon', 'Hercules', and 'Regency'.
Figure 22B:
Figure 22C:
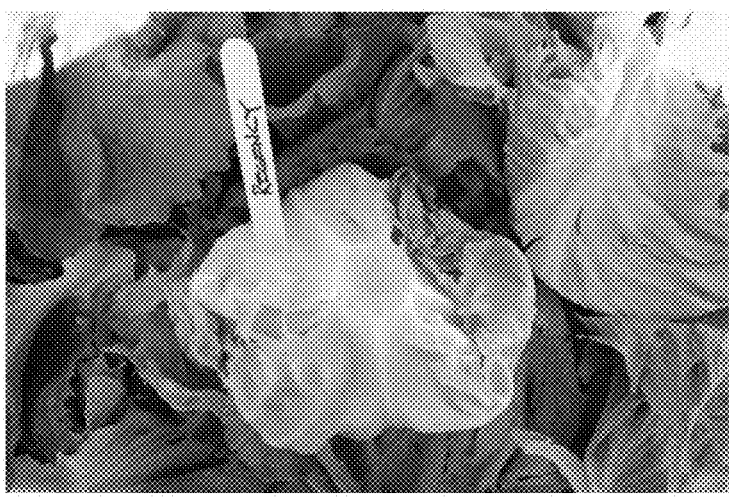
Figure 23A:
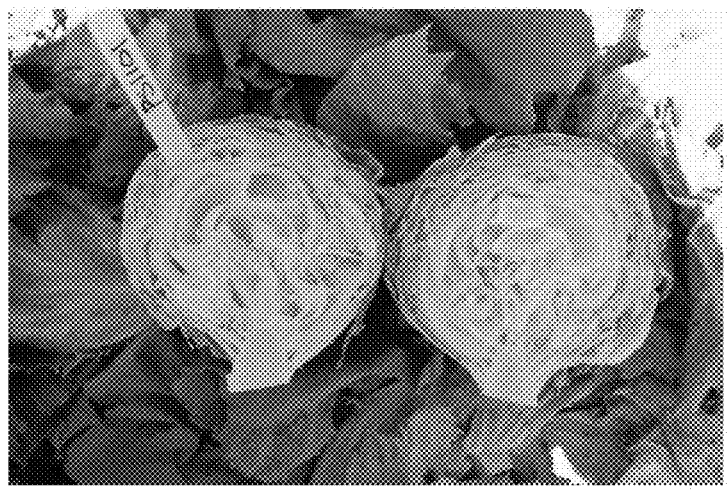
FIGS. 23A, 23B, and 23C show a comparison between lettuce varieties 'Canyon', 'Hercules', and 'Regency'.
Figure 23B:
Figure 23C:
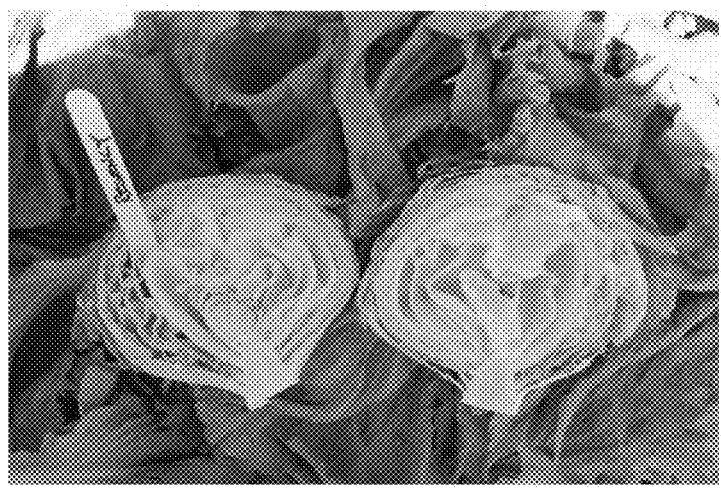
Figure 24A:
FIGS. 24A, 24B, and 24C show a comparison between lettuce varieties 'Canyon', 'Hercules', and 'Regency'.
Figure 24B:
Figure 24C:
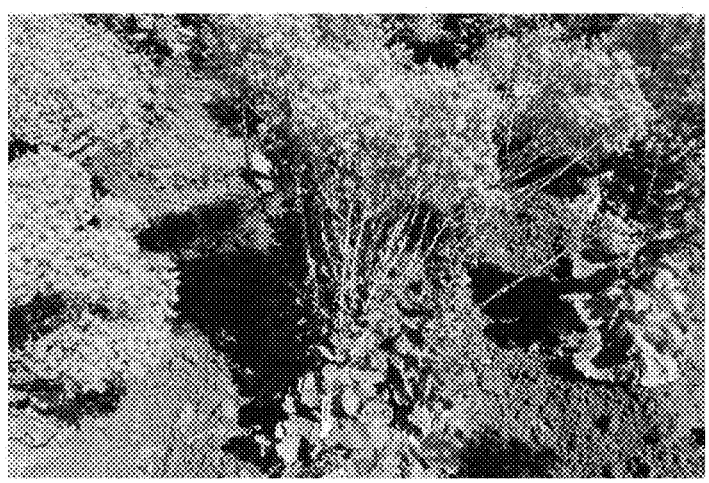
Figure 25A:
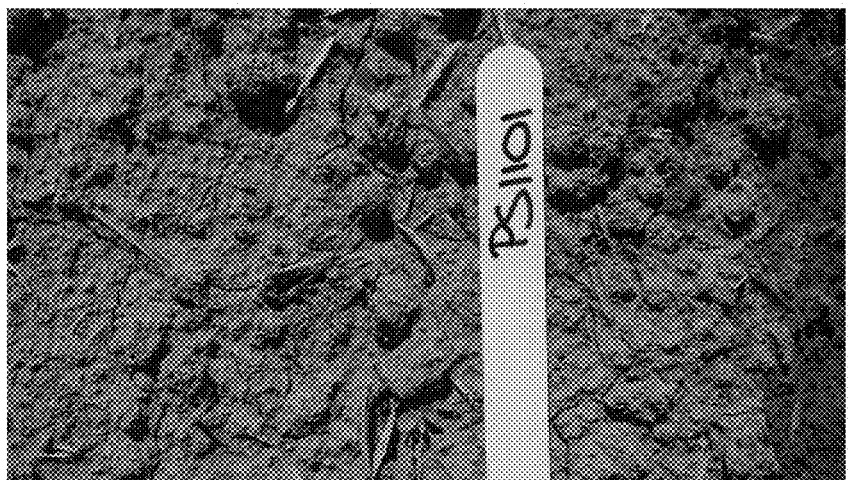
FIGS. 25A, 25B, and 25C show a comparison between lettuce varieties 'Canyon', 'Hercules', and 'Regency'.
Figure 25B:
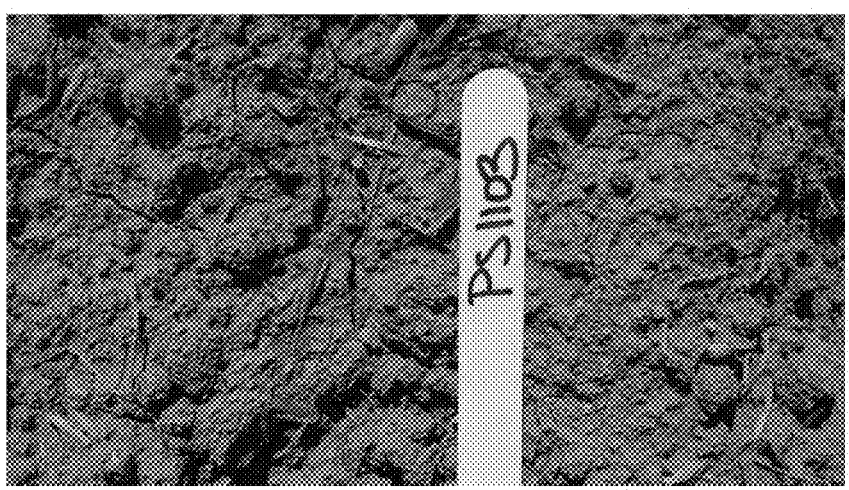
Figure 25C:
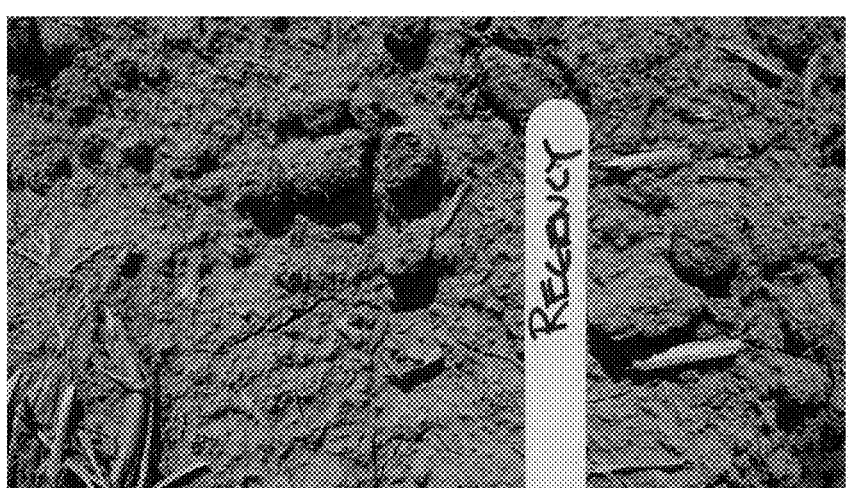
Figure 26A:
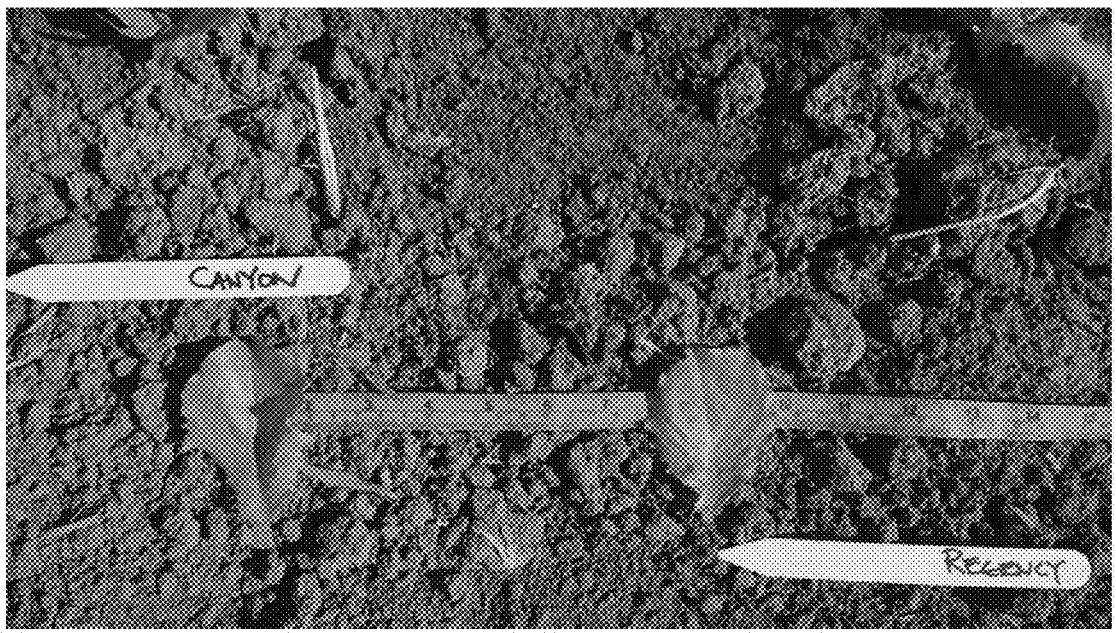
FIG. 26A shows a comparison of leaflets of lettuce varieties 'Canyon' and 'Regency'.
Figure 26B:
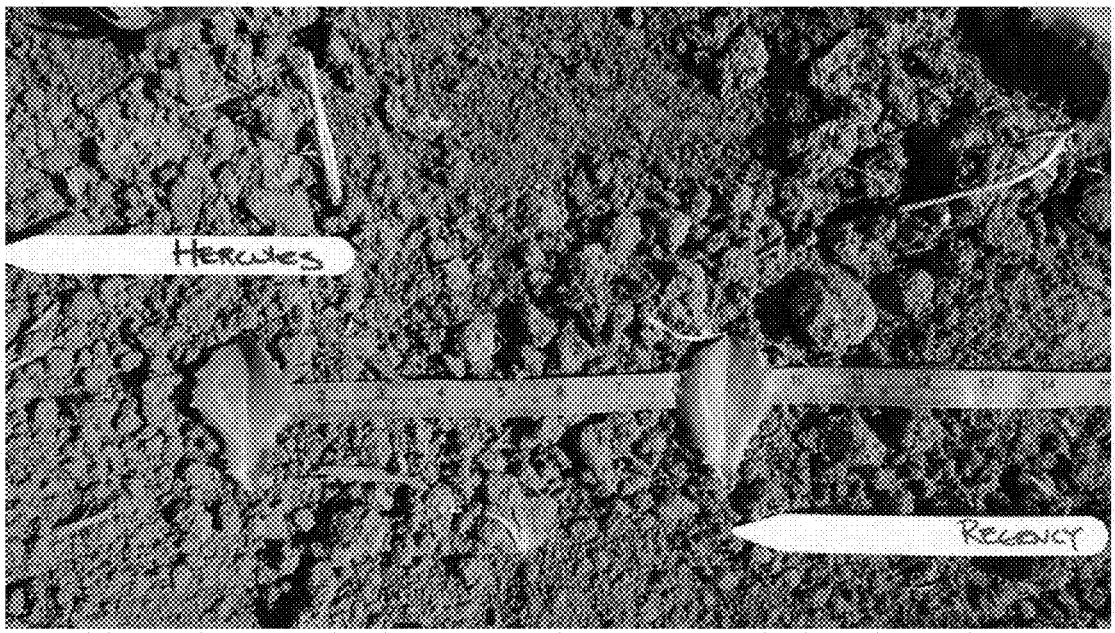
FIG. 26B shows a comparison of leaflets of lettuce varieties 'Hercules' and 'Regency'.

Further distinguishing features are apparent from the comparisons of the two varieties 'PS1102B' and 'Bondi' depicted in FIG. 18-20.

Objective Description of the Variety 'Hercules'

'Hercules' is an open-pollinated iceberg lettuce variety. This variety is distinct and unique to all other iceberg lettuce varieties due to its compact heading, larger frame, and darker leaf color. Lettuce variety 'Hercules' is the result of numerous generations of plant selections chosen for its compact heading, large frame, and dark leaf color.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Hercules'.

Lettuce variety 'Hercules' has the following morphologic and other characteristics:

Plant type: Crisp (i.e., iceberg)
Seed:
Color: White (e.g., comparable to 'Verpia')
Leaves:
Hue of green color of outer leaves: Greyish (e.g., comparable to 'Celtuce' and 'Du bon jardinier')
Anthocyanin coloration: Absent (e.g., comparable to 'Fiorella' and 'Sunrise')
Bolting:
Class: Medium (e.g., comparable to 'Carelia')
Disease/Pest Resistance:
Downy Mildew (*Bremia lactucae*) (Bl): Susceptible to Bl:2, Bl:5, Bl:7, Bl:12, Bl:14-Bl:18, Bl:20-Bl:26
Lettuce mosaic virus (LMV) strain Ls-1: Susceptible Pests:
*Nasonovia ribisnigri* biotype 0 (Nr:0): Susceptible
Comparisons to Commercial Lettuce Variety Table 17 below compares characteristics of lettuce variety 'Hercules' with the lettuce variety 'Regency'. Column 1 lists the characteristics, column 2 shows the characteristics for lettuce variety 'Hercules', and column 3 shows the characteristics for lettuce variety 'Regency'.

TABLE 17

| Characteristic | 'Hercules' | 'Regency' |
|---|---|---|
| Heading | Compact heading | Less compact heading |
| Frame | Larger framed | Smaller framed |
| Leaf color | Darker color | Lighter color |

Tables 18A and 18B below shows results of a first trial that compares the head weight, head diameter, and core length of 30 plants of lettuce variety 'Hercules' (Table 18A) with those of 30 plants of lettuce variety 'Regency' (Table 18B).

TABLE 18A

| 'Hercules' | Head Wt. | Head Diameter | Core Length |
|---|---|---|---|
| Max | 730 g | 165 mm | 50 mm |
| Min | 410 g | 120 mm | 35 mm |
| Average | 575 g | 145.83 mm | 43 mm |
| Std. Dev | 92.67 | 10.51 | 4.84 |

TABLE 18B

| 'Regency' | Head Wt. | Head Diameter | Core Length |
|---|---|---|---|
| Max | 800 g | 175 mm | 50 mm |
| Min | 360 g | 130 mm | 30 mm |
| Average | 585.5 g | 149.67 mm | 41.67 mm |
| Std. Dev | 98.03 | 9.82 | 5.14 |

Tables 19A and 19B below shows results of a second trial that compares the head weight, head diameter, core length, and frame diameter of 20 plants of lettuce variety 'Hercules' (Table 19A) with those of 20 plants of lettuce variety 'Regency' (Table 19B).

TABLE 19A

| 'Hercules' | Head Wt. | Head Diameter | Core Length | Frame Diameter |
|---|---|---|---|---|
| Max | 820 g | 155 mm | 45 mm | 50 cm |
| Min | 345 g | 100 mm | 25 mm | 39 cm |
| Average | 495.25 g | 135.75 mm | 34 mm | 44.7 cm |
| Std. Dev | 113.29 | 13.11 | 5.03 | 2.54 |

TABLE 19B

| 'Regency' | Head Wt. | Head Diameter | Core Length | Frame Diameter |
|---|---|---|---|---|
| Max | 750 g | 160 mm | 40 mm | 53 cm |
| Min | 405 g | 130 mm | 25 mm | 40 cm |
| Average | 548.75 g | 145.25 mm | 33.25 mm | 43.9 cm |
| Std. Dev | 74.50 | 9.80 | 5.45 | 3.94 |

Tables 20A and 20B below shows results of a third trial that compares the head weight, head diameter, core length, and circumference width of 30 plants of lettuce variety 'Hercules' (Table 20A) with those of 30 plants of lettuce variety 'Regency' (Table 20B).

TABLE 20A

| 'Hercules' | Head Wt. | Head Diameter | Core Length | Circumference |
|---|---|---|---|---|
| Max | 730 g | 150 mm | 50 mm | 19.5 in |
| Min | 345 g | 110 mm | 30 mm | 15.5 in |
| Average | 519.33 g | 133 mm | 39.5 mm | 17.54 in |
| Std. Dev | 94.26 | 11.03 | 5.144 | 0.82 |

TABLE 20B

| 'Regency' | Head Wt. | Head Diameter | Core Length | Circumference |
|---|---|---|---|---|
| Max | 710 g | 175 mm | 45 mm | 19.75 in |
| Min | 335 g | 120 mm | 30 mm | 15.5 in |
| Average | 498 g | 144.5 mm | 36.83 mm | 17.83 in |
| Std. Dev | 88.52 | 12.06 | 4.64 | 1.00 |

Tables 21A and 21B below shows results of a fourth trial that compares the head weight, head diameter, core length, circumference, and frame diameter of 20 plants of lettuce variety 'Hercules' (Table 21A) with those of 20 plants of lettuce variety 'Regency' (Table 21B).

TABLE 21A

| 'Hercules' | Head Wt. | Head Diameter | Core Length | Circumference | Frame Diameter |
|---|---|---|---|---|---|
| Max | 725 g | 145 mm | 50 mm | 19 in | 49 cm |
| Min | 345 g | 125 mm | 30 mm | 16.75 in | 34 cm |
| Average | 538 g | 137 mm | 38.25 mm | 17.81 in | 43.65 cm |
| Std. Dev | 97.51 | 6.96 | 4.94 | 0.58 | 3.94 |

TABLE 21B

| 'Regency' | Head Wt. | Head Diameter | Core Length | Circumference | Frame Diameter |
|---|---|---|---|---|---|
| Max | 810 g | 155 mm | 45 mm | 20 in | 50 cm |
| Min | 415 g | 115 mm | 25 mm | 16.5 in | 38 cm |
| Average | 564.25 g | 140 mm | 36.5 mm | 17.95 in | 44.3 cm |
| Std. Dev | 109.52 | 9.87 | 6.90 | 0.87 | 3.20 |

Further distinguishing features are apparent from the comparisons of the varieties 'Hercules', 'Canyon', and 'Regency' depicted in FIG. 21-26.

Objective Description of the Variety 'Canyon'

'Canyon' is an open-pollinated iceberg lettuce variety. This variety is distinct and unique to all other iceberg lettuce varieties due to its improved texture, earlier maturing time, earlier bolting, and lighter green color of leaves. Lettuce variety 'Canyon' is the result of numerous generations of plant selections chosen for its improved texture, early maturing time, early bolting, and light green color of leaves.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Canyon'.

Lettuce variety 'Canyon' has the following morphologic and other characteristics:
Plant type: Crisp (i.e., iceberg)
Seed:
Color: White (e.g., comparable to 'Verpia')
Leaves:
Hue of green color of outer leaves: Greyish (e.g., comparable to 'Celtuce' and 'Du bon jardinier')
Anthocyanin coloration: Absent (e.g., comparable to 'Fiorella' and 'Sunrise')
Bolting:
Class: Medium (e.g., comparable to 'Carelia')
Disease/Pest Resistance:
Downy Mildew (*Bremia lactucae*) (Bl): Susceptible to Bl:2, Bl:5, Bl:7, Bl:12, Bl:14-Bl:18, Bl:20-Bl:26
Lettuce mosaic virus (LMV) strain Ls-1: Susceptible
Pests:
*Nasonovia ribisnigri* biotype 0 (Nr:0): Susceptible
Comparisons to Commercial Lettuce Variety Table 22 below compares characteristics of lettuce variety 'Canyon' with the lettuce variety 'Regency'. Column 1 lists the characteristics, column 2 shows the characteristics for lettuce variety 'Canyon', and column 3 shows the characteristics for lettuce variety 'Regency'.

TABLE 22

| Characteristic | 'Canyon' | 'Regency' |
|---|---|---|
| Texture | Improved texture | Good texture |
| Time to maturity | Earlier maturing | Later maturing |
| Bolting | Earlier bolting | Later bolting |
| Color or leaves | Lighter green color | Darker green color |

Tables 23A and 23B below shows results of a first trial that compares the head weight, head diameter, and core length of 30 plants of lettuce variety 'Canyon' (Table 23A) with those of 30 plants of lettuce variety 'Regency' (Table 23B).

TABLE 23A

| 'Canyon' | Head Wt. | Head Diameter | Core Length |
|---|---|---|---|
| Max | 840 g | 160 mm | 50 mm |
| Min | 360 g | 120 mm | 25 mm |
| Average | 609.33 g | 146.5 mm | 41.33 mm |
| Std. Dev | 115.02 | 10.52 | 6.29 |

TABLE 23B

| 'Regency' | Head Wt. | Head Diameter | Core Length |
|---|---|---|---|
| Max | 800 g | 175 mm | 50 mm |
| Min | 360 g | 130 mm | 30 mm |
| Average | 585.5 g | 149.67 mm | 41.67 mm |
| Std. Dev | 98.03 | 9.82 | 5.14 |

Tables 24A and 24B below shows results of a second trial that compares the head weight, head diameter, core length, and frame diameter of 20 plants of lettuce variety 'Canyon' (Table 24A) with those of 20 plants of lettuce variety 'Regency' (Table 24B).

TABLE 24A

| 'Canyon' | Head Wt. | Head Diameter | Core Length | Frame Diameter |
|---|---|---|---|---|
| Max | 720 g | 160 mm | 45 mm | 49 cm |
| Min | 310 g | 120 mm | 25 mm | 39 cm |
| Average | 490.75 g | 141.75 mm | 35 mm | 42.85 cm |
| Std. Dev | 125.46 | 10.79 | 5.38 | 2.01 |

TABLE 24B

| 'Regency' | Head Wt. | Head Diameter | Core Length | Frame Diameter |
|---|---|---|---|---|
| Max | 750 g | 160 mm | 40 mm | 53 cm |
| Min | 405 g | 130 mm | 25 mm | 40 cm |
| Average | 548.75 g | 145.25 mm | 33.25 mm | 43.9 cm |
| Std. Dev | 74.50 | 9.80 | 5.45 | 3.94 |

Tables 25A and 25B below shows results of a third trial that compares the head weight, head diameter, core length, and circumference of 30 plants of lettuce variety 'Canyon' (Table 25A) with those of 30 plants of lettuce variety 'Regency' (Table 25B).

TABLE 25A

| 'Canyon' | Head Wt. | Head Diameter | Core Length | Circumference |
|---|---|---|---|---|
| Max | 690 g | 165 mm | 45 mm | 19.5 in |
| Min | 330 g | 110 mm | 30 mm | 16 in |
| Average | 507 g | 140.5 mm | 36.17 mm | 17.77 in |
| Std. Dev | 83.69 | 12.82 | 4.68 | 0.99 |

TABLE 25B

| 'Regency' | Head Wt. | Head Diameter | Core Length | Circumference |
|---|---|---|---|---|
| Max | 710 g | 175 mm | 45 mm | 19.75 in |
| Min | 335 g | 120 mm | 30 mm | 15.5 in |
| Average | 498 g | 144.5 mm | 36.83 mm | 17.83 in |
| Std. Dev | 88.52 | 12.06 | 4.64 | 1.00 |

Tables 26A and 26B below shows results of a fourth trial that compares the head weight, head diameter, core length, circumference, and frame diameter of 20 plants of lettuce variety 'Canyon' (Table 26A) with those of 20 plants of lettuce variety 'Regency' (Table 26B).

TABLE 26A

| 'Canyon' | Head Wt. | Head Diameter | Core Length | Circumference | Frame Diameter |
|---|---|---|---|---|---|
| Max | 715 g | 160 mm | 40 mm | 19 in | 48 cm |
| Min | 325 g | 110 mm | 20 mm | 15.5 in | 39 cm |
| Average | 551.5 g | 132.75 mm | 33.25 mm | 17.85 in | 43.35 cm |
| Std. Dev | 99.46 | 11.29 | 5.68 | 0.86 | 2.76 |

TABLE 26B

| 'Regency' | Head Wt. | Head Diameter | Core Length | Circumference | Frame Diameter |
|---|---|---|---|---|---|
| Max | 810 g | 155 mm | 45 mm | 20 in | 50 cm |
| Min | 415 g | 115 mm | 25 mm | 16.5 in | 38 cm |
| Average | 564.25 g | 140 mm | 36.5 mm | 17.95 in | 44.3 cm |
| Std. Dev | 109.52 | 9.87 | 6.90 | 0.87 | 3.20 |

Further distinguishing features are apparent from the comparisons of the varieties 'Hercules', 'Canyon', and 'Regency' depicted in FIG. 21-26.

Further Embodiments

Breeding

In lettuce breeding, lines are selected for their appropriate characteristics. For example, one line may be selected for bolt tolerance in the fall growing conditions of the desert production locations of California and Arizona. Another line may be selected for the size, color, and texture of the lettuce head. Crosses are made, for example, to produce a dark green, sure heading iceberg lettuce with improved texture, and size for fall plantings in Yuma, Ariz. and Huron, Calif.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possibilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 2-3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art.

Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

Deposit Information

Lettuce variety 'Haymaker'

A deposit of the lettuce variety 'Haymaker' is maintained by Pinnacle Seed, Inc., having an address of P.O. Box 222672, Carmel, Calif. 93923, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

The lettuce variety 'Haymaker' was deposited on May 4, 2018 according to the Budapest Treaty in the American Type Culture Collection (ATCC), ATCC Patent Depository, 10801 University Boulevard, Manassas, Va., 20110, USA. The deposit has been assigned ATCC number PTA-125104. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

Lettuce variety 'Hercules'

A deposit of the lettuce variety 'Hercules' is maintained by Pinnacle Seed, Inc., having an address of P.O. Box 222672, Carmel, Calif. 93923, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

The lettuce variety 'Hercules' was deposited on Oct. 17, 2019 according to the Budapest Treaty in the American Type Culture Collection (ATCC), ATCC Patent Depository, 10801 University Boulevard, Manassas, Va., 20110, USA. The deposit has been assigned ATCC number PTA-126296. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

What is claimed:

1. A *Lactuca sativa* seed designated as 'Hercules', representative sample of seed having been deposited under ATCC Accession Number PTA-126296.

2. A *Lactuca sativa* plant produced by growing the seed of claim 1.

3. A plant part from the plant of claim 2.

4. The plant part of claim 3, wherein said part is a head, a leaf, or a portion thereof.

5. The plant part of claim 4, wherein said part is a head.

6. A *Lactuca sativa* plant having all the physiological and morphological characteristics of the *Lactuca sativa* plant of claim 2.

7. A plant part from the plant of claim 6.

8. The plant part of claim 7, wherein said part is a head, a leaf, or a portion thereof.

9. The plant part of claim 8, wherein said part is a head.

10. An $F_1$ hybrid *Lactuca sativa* plant having 'Hercules' as a parent where 'Hercules' is grown from the seed of claim 1.

11. A pollen grain or an ovule of the plant of claim 2.

12. A tissue culture of the plant of claim 2.

13. A lettuce plant regenerated from the tissue culture of claim 12, wherein the plant has all of the morphological and physiological characteristics of a lettuce plant produced by growing seed designated as 'Hercules', representative sample of seed having been deposited under ATCC Accession Number PTA-126296.

14. A method of making lettuce seeds, said method comprising crossing the plant of claim 2 with another lettuce plant and harvesting seed therefrom.

15. A method of selecting lettuce variety 'Hercules', comprising:
   a) growing more than one plant from the seed of claim 1; and
   b) selecting a plant from step a).

16. A *Lactuca sativa* plant selected by the method of claim 15.

17. *Lactuca sativa* seed produced from the *Lactuca sativa* plant of claim 16.

* * * * *